US012721751B2

(12) United States Patent
Keller

(10) Patent No.: US 12,721,751 B2
(45) Date of Patent: Sep. 1, 2026

(54) SUPERELASTIC NITINOL RING FOR CATARACT CAPSULOTOMY

(71) Applicant: Centricity Vision, Inc., Carlsbad, CA (US)

(72) Inventor: Christopher Guild Keller, El Cerrito, CA (US)

(73) Assignee: Centricity Vision, Inc., Carlsbad, CA (US)

( * ) Notice: Subject to any disclaimer, the term of this patent is extended or adjusted under 35 U.S.C. 154(b) by 208 days.

(21) Appl. No.: 18/777,423

(22) Filed: Jul. 18, 2024

(65) Prior Publication Data

US 2025/0025338 A1 Jan. 23, 2025

Related U.S. Application Data

(60) Provisional application No. 63/514,861, filed on Jul. 21, 2023.

(51) Int. Cl.
*A61F 9/007* (2006.01)

(52) U.S. Cl.
CPC ................................ *A61F 9/00754* (2013.01)

(58) Field of Classification Search
CPC .......... A61F 9/0075; C22F 1/10; C22F 1/006; A61B 2018/00601; A61B 2018/00321; A61B 2017/00526; C21D 1/26
USPC ........................................................... 606/27
See application file for complete search history.

(56) References Cited

U.S. PATENT DOCUMENTS 8,702,698 B2 4/2014 Keller
9,125,720 B2 9/2015 Jia et al.
9,173,771 B2 11/2015 Keller
9,254,224 B2 2/2016 Keller
9,271,868 B2 3/2016 Keller
9,456,923 B2 10/2016 Keller
9,861,523 B2 1/2018 Keller
10,070,989 B2 9/2018 Keller
10,206,816 B2 2/2019 Keller
10,278,760 B2 5/2019 Keller
10,285,855 B2 5/2019 Keller
10,363,167 B2 7/2019 Keller
10,736,777 B2 8/2020 Keller
11,058,579 B2 7/2021 Keller
11,406,439 B2 8/2022 Keller
11,426,308 B2 8/2022 Keller
(Continued)

OTHER PUBLICATIONS

PCT International Search Report and Written Opinion, PCT Application No. PCT/US2024/038609, Oct. 21, 2024, nine pages.

*Primary Examiner* — Beverly M Flanagan
(74) *Attorney, Agent, or Firm* — Fenwick & West LLP

(57) ABSTRACT

A method for manufacturing a super elastic nitinol ring. The method includes compressing a nitinol wire on a first side and a second side to produce permanently flattened edges and cutting off a portion of the nitinol wire on a third side and a fourth side to produce flattened edges. The method includes producing a modified nitinol wire with a rectangular cross section formed by the flattened edges on the four sides, bending the modified nitinol wire into a ring shape such that a first end of the modified nitinol wire aligns with a second end of the modified nitinol wire; and permanently coupling the first end to the second end to produce a nitinol ring. The nitinol ring is coupled to a capsulotomy device such that the nitinol ring, upon receiving current flow from the capsulotomy device, produces heat sufficient to cut tissue in contact with the nitinol ring.

20 Claims, 21 Drawing Sheets

100

(56) References Cited

U.S. PATENT DOCUMENTS

| | | | |
|---|---|---|---|
| 11,596,547 | B2 | 3/2023 | Keller et al. |
| 11,596,548 | B2 | 3/2023 | Keller |
| 11,596,549 | B2 | 3/2023 | Keller et al. |
| 2022/0378614 | A1 | 12/2022 | Keller |
| 2023/0014011 | A1 | 1/2023 | Filice et al. |

SUPERELASTIC NITINOL RING FOR CATARACT CAPSULOTOMY

CROSS-REFERENCE TO RELATED APPLICATIONS

This application claims the benefit of U.S. Provisional Application No. 63/514,861, filed Jul. 21, 2023, which is incorporated by reference in its entirety.

BACKGROUND

This description generally relates to medical devices and specifically to microsurgical instruments for capsulotomies. Cataracts are the leading cause of surgically curable blindness in the world. In a cataract, the lens of the eye has defects that scatter light so that vision is impaired. The lens is fully enclosed by a collagen membrane about 0.015 to 0.020 millimeters (mm) thick, called the "lens capsule". During the surgical cataract procedure, a hole (called a "capsulotomy") is made on the anterior side of the lens capsule to allow the surgeon to remove the defective natural lens, and to insert an artificial lens through this hole. The remaining part of the lens capsule (also called the capsular bag) serves to hold the new artificial lens (called an Intra Ocular Lens, abbreviated IOL) for the rest of the patient's life. The excised circular patch of membrane is discarded. The capsulotomy is supposed to be centered on the visual axis of the eye. It is generally 5.0 to 5.5 mm in diameter (but may range from 4.0 mm to 6.0 mm depending on the surgeon's preference). The capsulotomy should be circular and have smooth edges that are free of defects. Defects are weak points from which tears in the membrane can initiate.

A challenge with current nitinol rings in capsulotomy devices is that a super elastic nitinol ring is difficult and expensive to produce. When the surgical discharge of electrical current is passed through the ring, it is important to have a uniform current density around the ring so that it heats uniformly. Otherwise, there may be hot spots and cold spots. If there are hot or cold spots due to nonuniformity of heating in the ring, defects in the capsulotomy edge can occur that are vulnerable to initiating significant tears in the capsular bag. The capsular bag should remain intact, without tears, in order to hold the IOL properly.

SUMMARY

Embodiments relate to a microsurgical device for tissue cutting that produces consistent capsulotomies and improves upon current tissue cutting device. In particular, the disclosure provides a method for manufacturing a super elastic nitinol ring for a cataract capsulotomy. The method includes compressing a nitinol wire on a first side of the nitinol wire and a second side of the nitinol wire to produce permanently flattened edges on the first side and the second side of the nitinol wire of at least a threshold width. The nitinol wire has a circular cross section, and the first side is opposite the second side of the nitinol wire. The method may include cutting off a portion of the nitinol wire on a third side of the nitinol wire and a fourth side of the nitinol wire to produce flattened edges on the third side and the fourth side of the nitinol wire of at least a threshold height. The third side is opposite to the fourth side of the nitinol wire. The method further includes producing a modified nitinol wire with a rectangular cross section formed by the flattened edges on the first side, second side, third side and fourth side, bending the modified nitinol wire into a ring shape such that a first end of the modified nitinol wire aligns with a second end of the modified nitinol wire, and permanently coupling the first end to the second end to produce a nitinol ring. The nitinol ring is coupled to a capsulotomy device such that the nitinol ring, upon receiving current flow from the capsulotomy device, produces heat sufficient to cut tissue in contact with the nitinol ring.

BRIEF DESCRIPTION OF THE DRAWINGS

FIG. 6 illustrates another example system for performing a capsulotomy, according to one embodiment.

Figure 1A:
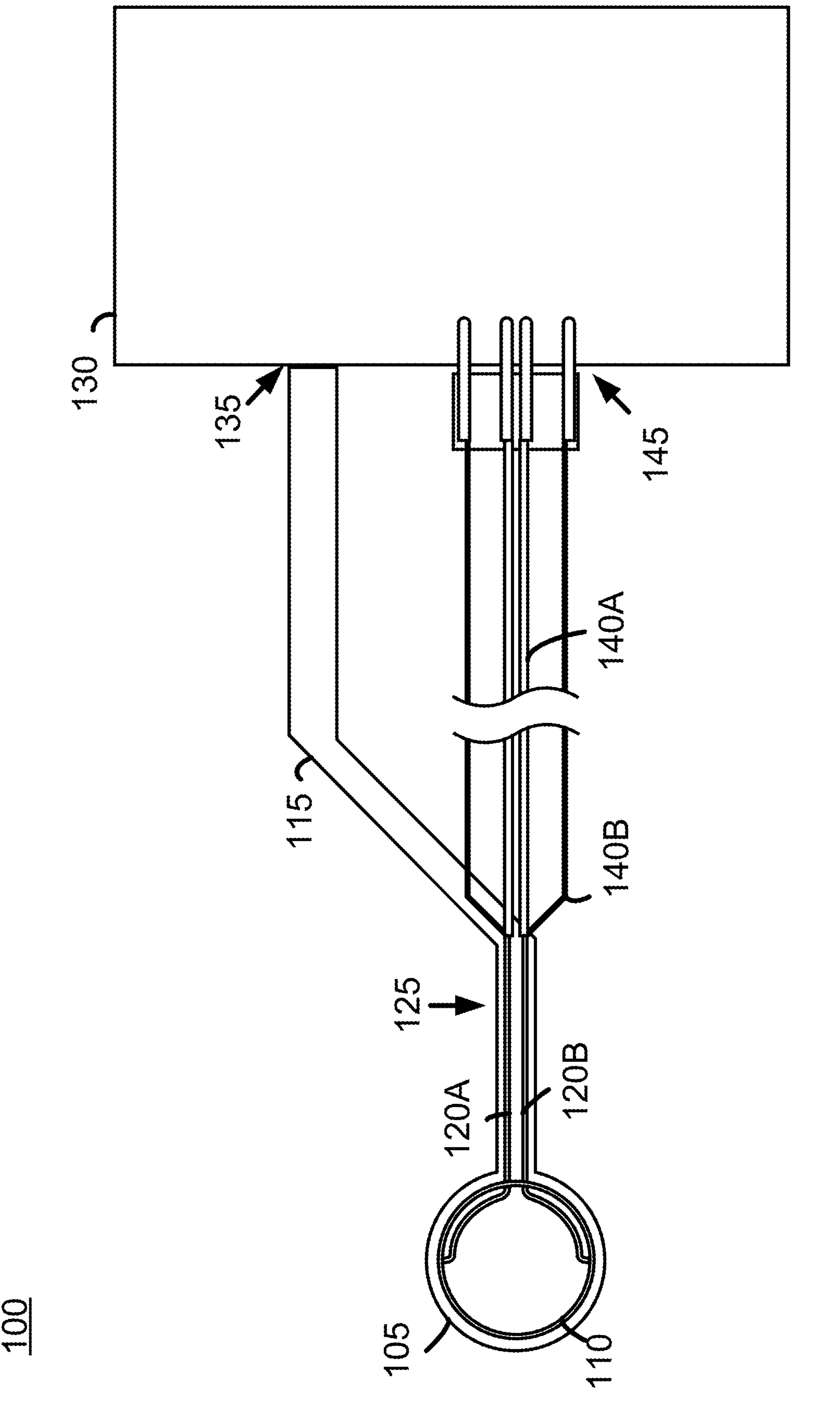
FIG. 1A illustrates a microsurgical device connected to its control console, according to one embodiment.

The figures depict various example embodiments of the present technology for purposes of illustration only. One skilled in the art will readily recognize from the following description that other alternative embodiments of the structures and methods illustrated herein may be employed without departing from the principles of the technology described herein.

DETAILED DESCRIPTION

Embodiments described herein relate to a nitinol ring design that provides a lower cost structure for the electrically heated super elastic ring used in cutting the capsulotomy on the anterior lens capsule of an eye for cataract surgery. The mechanism of the cutting process by which the nitinol ring cuts the capsular membrane is through the combined action of several effects. In some embodiments, a silicone suction cup applies suction that stretches the capsular membrane, pulling it further within the inner diameter (ID) of the nitinol ring, and pulling it up into forcible contact with the ID edge and/or the bottom surface of the ring, so that the circle where the cut will be placed is in a state of high tensile mechanical stress. After suction has developed, an electrical current may flow in the ring to quickly heat the ring above the critical temperature of water (374° C.) so that the water near the ring immediately turns to steam (there may be no lag time for bubbles to nucleate: the phase change from liquid to vapor is immediate). The entire heating process may be performed in 0.001 to 0.004 seconds or less. On this time scale, the hot steam does not have time to escape from between the ring and the capsular membrane due to the inertial confinement imposed by the mass of the surrounding material. As a result of this confinement, the trapped steam achieves a high pressure that lasts long enough to cut through the membrane. Forces from the initial state of mechanical tensile stress and from the pressure of the steam, plus the high temperature acting to weaken and melt the capsule, combine to cut through the capsule nearly instantaneously over the full 360 degree circle. The free-floating circular patch of excised membrane may be removed and discarded. Since the process is fast and is highly localized, very little heat energy is needed to cut the membrane. There is no effect on neighboring tissues because no significant heat is left over to conduct away from the site of the cut. If there are hot or cold spots due to nonuniformity of heating in the ring, defects in the capsulotomy edge can occur, causing significant tears in the capsular bag.

Convectional method of manufacturing nitinol rings may include cutting nitinol rings from nitinol tubing. However, the process of drawing tubing does not always produce a uniform wall thickness throughout the tube. When a ring is cut from such tubing, it will have a larger cross-sectional area of current carrying metal where the wall is thicker, and a smaller cross-sectional area where the wall is thinner. In use, locations with large cross-sectional areas will have a lower current density and may become cold spots, and locations with small cross-sectional areas will have higher current density and may become hot spots. Other methods for making nitinol tubing may include, e.g., sputtering nitinol onto rotating mandrels. This method can produce tubing with very tight wall thickness tolerances, but it is a prohibitively expensive process.

The present disclosure provides a method of using nitinol wire for manufacturing a nitinol ring. Nitinol wires can be drawn to very close diametrical tolerances (e.g., +/−0.0001 inch or +/−0.00254 mm) in a round cross section at low cost. Immediately after the process of drawing the nitinol through a die to set its diameter, the material is not super elastic because it has been plastically deformed and is martensitic. To make nitinol super elastic, it can be thermally annealed (typically at a temperature that may range from about 450° C. to 650° C.) so that it can become austenitic in crystal structure. To make the ring from the wire, an option is to work on the wire while it is still in the easily deformable non-super-elastic state (martensitic state), and then after all mechanical forming, welding, and grinding is done, the finished structure can be annealed to make the metal austenitic and super elastic.

In some embodiments, super elastic nitinol wire may be produced in the form of rectangular cross section wire, and in other embodiments, other shapes (such as circular, semi-rectangular, and the like) may be formed. The dimensional tolerances for the cross-sectional area of the wire may be held very tightly, so that when the ring is in use and an electrical heating current is made to flow through the wire, the current density will be the same everywhere throughout the wire. The even current density allows the heating of the structure to be uniform. The uniformity of the cross-sectional area of wires may create a low-cost design that heats uniformly to cut a membrane, for example the anterior capsular membrane, of a lens of an eye in cataract surgery. Embodiments are shown in which the body of the ring is made from a single high aspect ratio (height/width) wire, or round wires welded together in a stack (with the planes of the rings parallel to each other) to provide the aspect ratio necessary for high stiffness in the vertical direction and low stiffness in-plane, so that the ring may be stretched for insertion into the eye. The term “plane of the ring” means the plane that contains the circular cutting edge of the ring. This plane is perpendicular to the direction in which ring height is measured, and parallel to any of the radial directions in which ring wall thickness is measured.

Figure 1B:
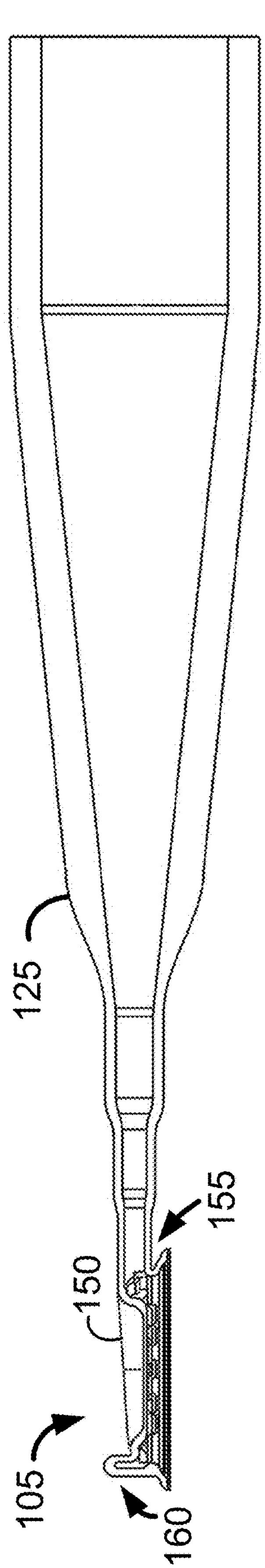
FIGS. 1B-1C illustrate cross-sectional views of the microsurgical device shown in FIG. 1A, according to one embodiment.
Figure 1B:
Figure 1C:
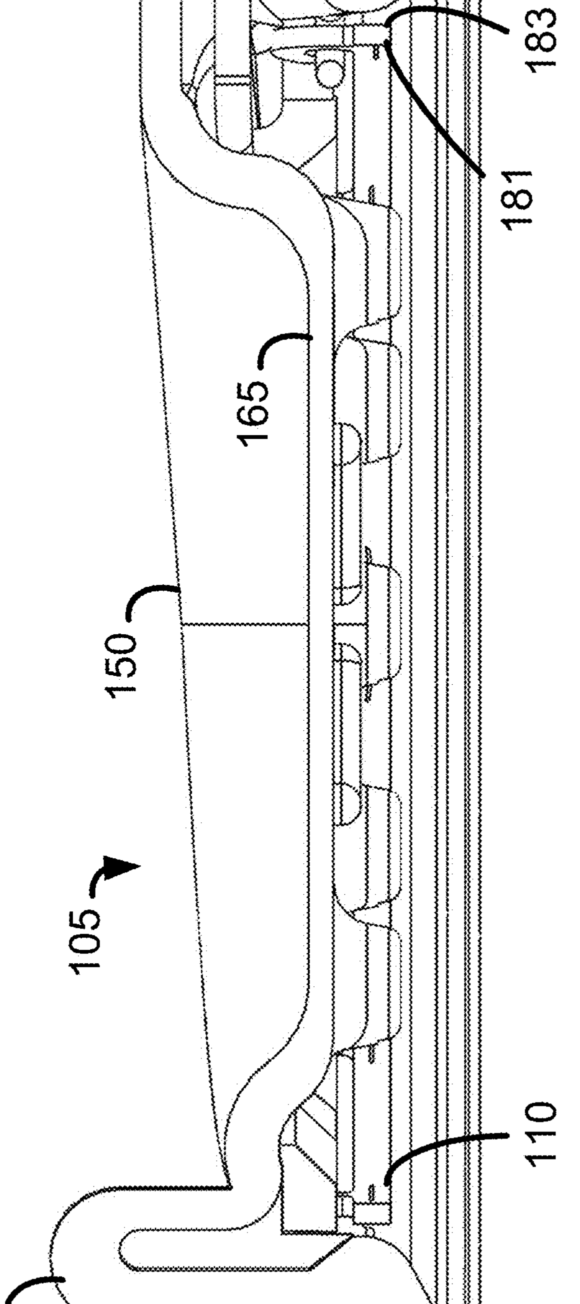
Figure 1D:
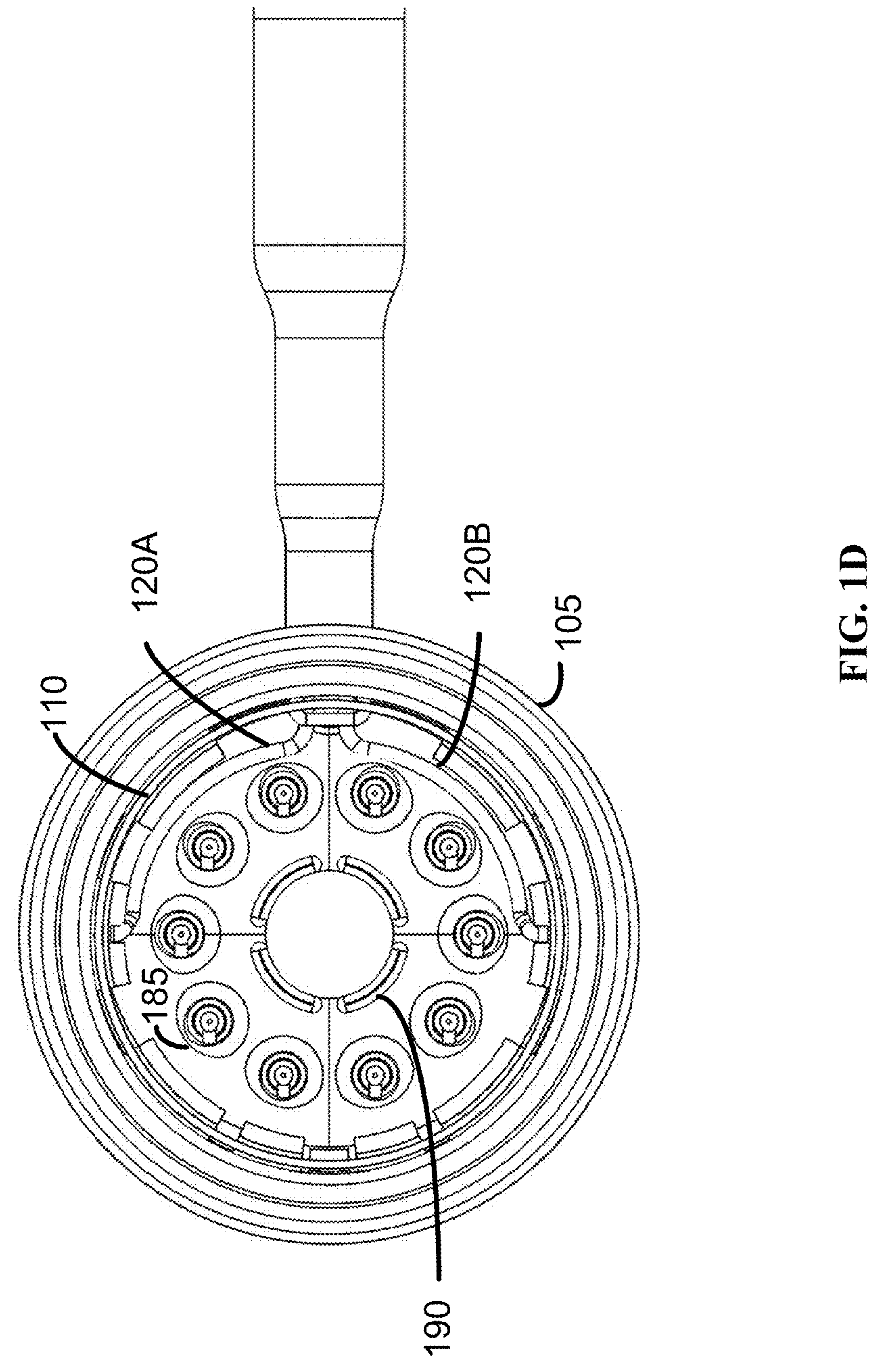
FIG. 1D illustrates a bottom view of the microsurgical device shown in FIG. 1A, according to one embodiment.
Figure 1E:
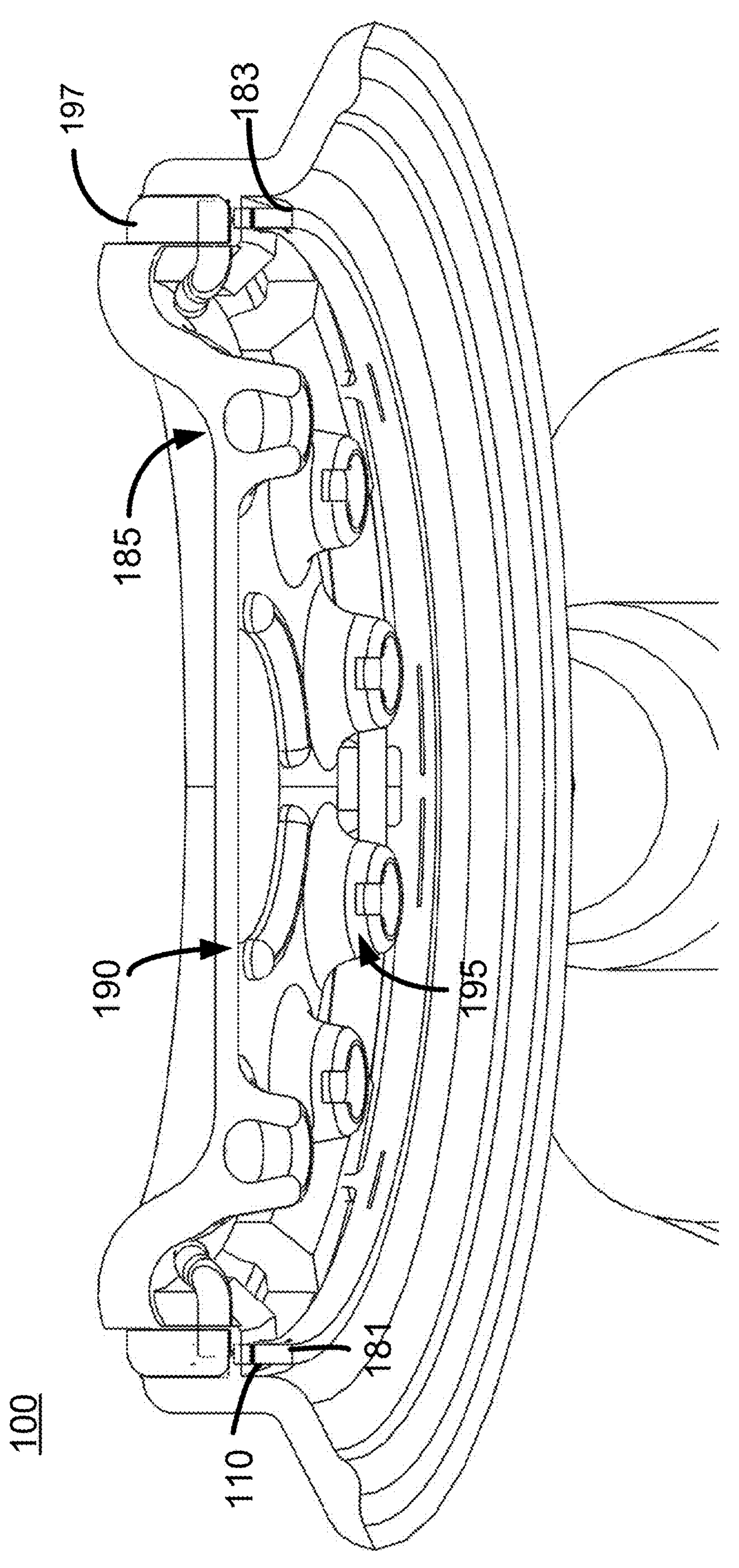
FIG. 1E illustrates a bottom perspective view of the microsurgical device shown in FIG. 1A, according to one embodiment.
Figure 1F:
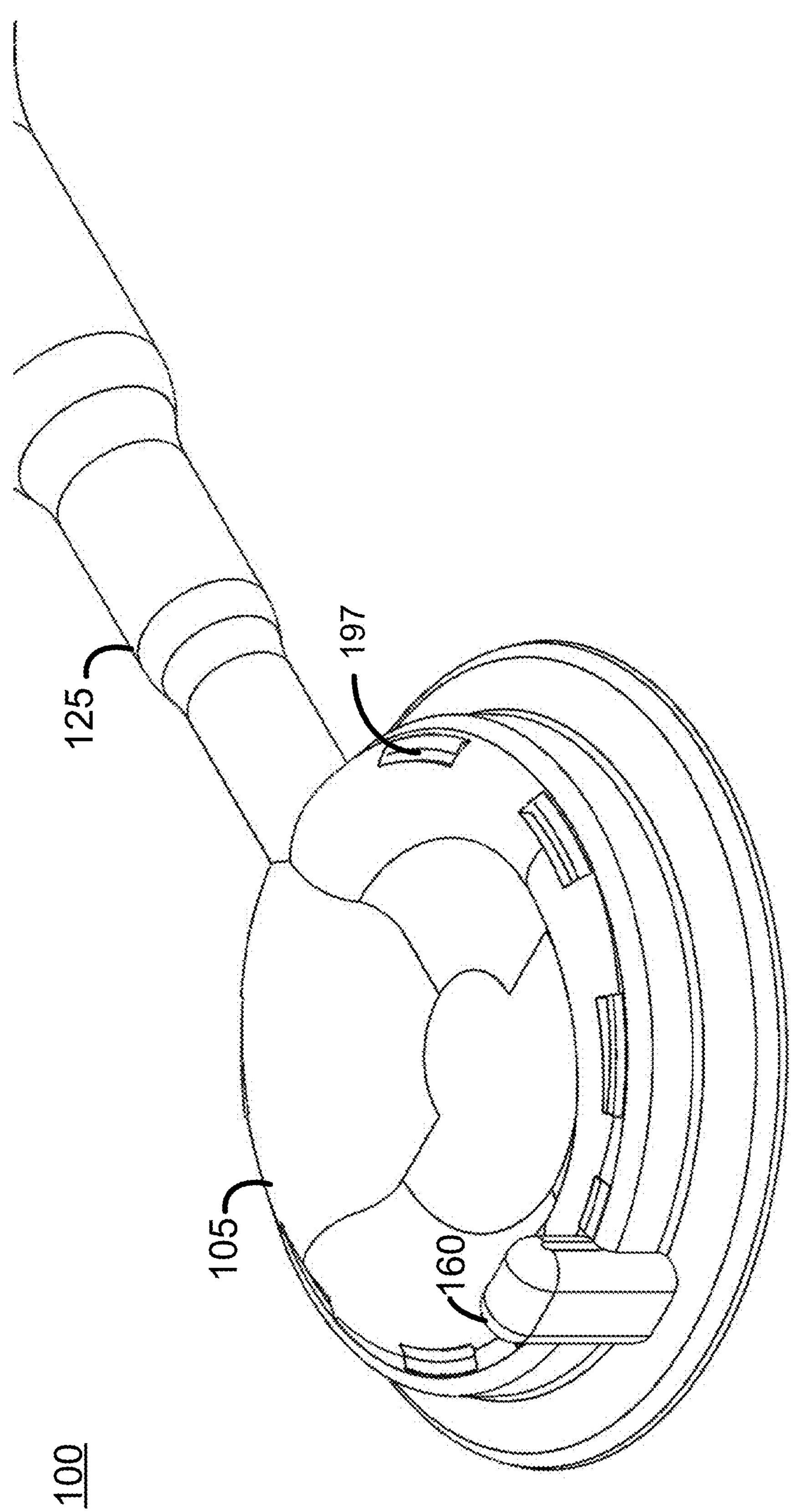
FIG. 1F illustrates a top perspective view of the microsurgical device shown in FIG. 1A, according to one embodiment.

FIGS. 1A-1F illustrate various views of a microsurgical device 100 for tissue cutting. FIG. 1A illustrates an embodiment of a microsurgical device 100. FIGS. 1B-1C illustrate cross-sectional views of the microsurgical device 100. FIG. 1D illustrates a bottom view of the microsurgical device 100. FIG. 1E illustrates a bottom perspective view of the microsurgical device 100. FIG. 1F illustrates a top perspective view of the microsurgical device 100.

The device 100 shown in FIG. 1A includes a suction cup 105, a cutting element 110 (also referred to as “cutting ring” herein), one or more suction tubes 115, electrical leads 120A, 120B, and a stem 125. The suction cup 105 and cutting element 110 are located at a distal end of the stem 125, which houses the one or more suction tubes 115 and the electrical leads 120A, 120B. The device 100 further includes a control console 130 (also referred to as “controller” herein) that is configured to provide suction to the suction cup 105 and electrical energy to the cutting element 110. The suction cup 105 is connected to the control console 130 via the one or more suction tubes 115 and a suction connector 135. The cutting element 110 is connected to the control console 130 via the electrical leads 120A, 120B, one or more sets of electrical conductors, such as electrical conductors 140A, 140B, and an electrical connector 145.

The suction cup 105 is a foldable structure that can provide a water-tight seal between the edges of the suction cup 105 and the tissue being excised (e.g., lens capsule, corneal tissue, connective tissue, and the like). Because of the fluidic seal between the suction cup 105 and the tissue, vacuum or fluidic pressure can be applied to the suction cup 105 and the tissue so that the resulting pressure presses the cutting element 110 against the tissue. Pressing the cutting element 110 against the tissue facilitates a more precise, smoother cut. The foldable structure of the suction cup 105 is reversibly collapsible such that a cross-section of the suction cup 105 can decrease for insertion of the device 100 through an incision. As such, the suction cup 105 may include a compliant material, such as silicone, polyurethane, and the like. In one embodiment, the material of the suction cup 105 is a medical grade silicone having a Shore A durometer of 60 (e.g., Nusil MED-4960). Further, the silicone may be clear, which may assist in the placement of the suction cup 105.

The cutting element 110 is an element designed to cut tissue through application of pressure and/or electrical current via one or more electrical leads 120A, 120B coupled to the cutting element 110. The cutting element 110 can be made from various materials. In some embodiments, the metallic components of the cutting element 110 may be made by electroforming suitable materials such as nickel, nickel-titanium alloys, gold, steel, copper, platinum, iridium, molybdenum, tantalum, and the like. When the cutting element 110 is configured to electrically excise tissue, the material for the cutting element 110 is electrically conductive. In addition, the cutting element 110 is reversibly collapsible such that a cross-section of the cutting element 110 can decrease for insertion of the device 100 through an incision. Therefore, the material of the cutting element 110 is generally elastic so that it can return to its original shape after insertion of the device 100 through the incision. A typical construction example is a superelastic nitinol ring having a wall thickness of 0.075 mm, height of 0.140 mm, and tabs. Another strategy is to add to this superelastic body a thin film (e.g., 0.0001 to 0.002 mm) of a more conductive material that does not have to be superelastic because it is very thin. Examples of materials include, but are not limited to, spring steel, stainless steel, titanium nickel alloy, graphite, nitinol, nickel, nickel-chrome alloy, tungsten, molybdenum, tantalum, gold, silver, or any other material that will allow the cutting element 110 to return to its prior shape.

The device 100 is capable of delivering a wide range of energies (e.g., from 0 to 3 joules, or more) via the cutting element 110. The energy dissipated by the cutting element 110 during use in surgery may be determined empirically through use on a specific tissue of interest. For example, in a capsulotomy of the anterior lens capsule of an adult human, it was found that about 1.2 joules produced a satisfactory result. Some specific example of applications to lens capsulotomies include pediatric as well as adult humans and other animals such as dogs, listed in order of increasing energy need. To accommodate the varying energy needs, the amount of energy dissipated by the cutting element 110 may be controlled by controlling parameters such as the number of pulses, duration of each pulse, time between pulses, and/or energy of each pulse applied to the tissue via the cutting element 110. These parameters may be determined empirically for each tissue application and/or via computational modeling. In addition, temperature gradients in the cutting element 110 may be designed and/or modified for different tissues.

The one or more suction tubes 115 are located within the stem 125 of the device 100. The one or more suction tubes 115 are configured to provide suction to the suction cup 105. The one or more suction tubes 115 provide suction to the suction cup 105 to compress the suction cup 105 against the tissue being excised. The one or more suction tubes 115 may also be configured to reverse the suction and/or fluid flow being applied to the suction cup 105 to disengage the suction cup 105 and cutting element 110 from the excised tissue. In some embodiments, the material of the suction tubes 115 is a medical grade silicone having a Shore A durometer of 60 (e.g., Nusil MED-4960). In some embodiments, the electrical leads 120A, 120B, an anchor thread, and/or a rigid extender run through the one or more suction tubes 115 to the suction cup 105.

The one or more suction tubes 115 may be further configured to act as fluid paths. For example, the one or more suction tubes 115 may be primed before use with a solution, such as a balanced salt solution. Priming the fluid paths of the one or more suction tubes 115 may help ensure that there is little to no compressible air in the device 100. In addition, after excision of the tissue is complete, a hydraulic release of the one or more suction tubes 115 may be performed to release the suction cup 105 from the tissue. In some embodiments, the hydraulic release consists of forcing 0.05 ml to 0.2 ml of a balanced salt solution from the suction tubes 115 back into the suction cup 105.

The configuration of the one or more suction tubes 115 along the inner surface of the suction cup 105 may vary. For example, when there are two or more suction tubes 115, the suction tubes 115 may be located at antipodal points of the suction cup 105. This configuration may ensure equal distribution of suction throughout the suction channels of the suction cup 105. In other embodiments, the suction tubes 115 may be adjacent, located within a threshold number of degrees of each other, located within a threshold distance of each other, and the like. Further, the suction tubes 115 may be located along an outer surface of the suction cup 105, along a bottom surface of the suction cup 105, along a top surface of the suction cup 105, and the like. In embodiments where the device 100 includes a single suction tube 115, the suction tube may be located at any point along the inner surface of the suction cup 105. For example, an orifice of the suction tube 115 may be located in a roof of the suction cup 105, at a proximal end of the suction cup 105, at a distal end of the suction cup 105, and the like.

The electrical leads 120A, 120B are configured to provide electrical energy to the cutting element 110. The electrical leads 120A, 120B are located within the stem 125 of the device 100 and coupled to a surface of the cutting element 110. In some embodiments, the electrical leads 120A, 120B are silver wires. In other embodiments, the electrical leads 120A, 120B are made of copper, aluminum, gold, or the like. In addition, the electrical leads 120A, 120B may insulated.

The control console 130 is configured to provide suction to the suction cup 105 and electrical energy to the cutting element 110. In addition, an operator of the device 100 may control the depth of cut via the control console 130 by modifying the suction and/or electrical parameters of the device 100.

Suction is provided to the suction cup 105 via one or more suction tubes 115 connected to the control console 130 and a suction connector 135. Using the control console 130, an operator of the device 100 may provide suction to the suction cup 105, reverse suction during disengagement of the device 100, and/or flush the fluid paths of the one or more suction tubes 115 with a solution. In addition, an operator of the device 100 may modify the amount of suction applied to the suction cup 105 based on the operation being performed. In some embodiments, an operator of the device 100 may manually modify the amount of suction applied to the suction cup 105, for example using a vacuum valve and/or a vacuum gauge of the control console 130. Alternatively, or additionally, the control console 130 may include predetermined suction parameters determined via experimentation, modeling, and/or a combination thereof that are each associated with a procedure. In addition, using the control console 130, different amounts of suction may be provided to different suction tubes. By way of example, suction pressure of 19+/−1 inch of Hg vacuum has been used successfully. That is gauge pressure, not absolute pressure, so the same pressure differential is established by the control console 130 across the suction cup wall regardless of altitude at which it is used. Further, as described below, the pressure applied may be fluidic pressure.

The control console 130 delivers electrical energy to the cutting element 110 via the electrical leads 120A, 120B, one or more sets of electrical conductors 140A, 140B, and an electrical connector 145. A first set of electrical conductors 140A may be configured to provide power to the cutting element 110. A second set of electrical conductors 140B may be for resistance measurement and may be connected to a measurement device, such as a Kelvin probe (also known as the 4-wire resistance measurement method). In some embodiments, the first set of electrical conductors 140A and/or the second set of electrical conductors 140B are copper wires, such as (respectively) 24 ga copper wires, 30 ga copper wires, and the like. In other embodiments, the first set of electrical conductors 140A and/or the second set of electrical conductors 140B are composed of aluminum, gold, silver, or the like. Electrical energy may be provided to the cutting element 110 as one or more electrical waveforms. The one or more electrical waveforms are discharged through the cutting element 110 to cause the cutting element 110 to heat up for a short time, such as 0.0001 seconds to 0.05 seconds, depending on the applied voltage and current.

Using the control console 130, the depth of cut may be controlled by controlling the amount of electrical discharge applied to the cutting element 110. For example, the depth of cut may be controlled by modifying one or more of: the energy of each pulse, the number of pulses in the pulse train, the inter-pulse intervals, and the like. As with the suction, these parameters may be manually modified by an operator of the device 100 using control elements of the control console 130. Alternatively, or additionally, the control console 130 may include predetermined sets of parameters that are each associated with different depths of cut, different patient types, and the like. These sets of parameters may be determined through experimentation, modeling, and/or a combination thereof. The control console 130 may be a controller, microprocessor, a programmable hardware logic, etc.

In some embodiments, the control console 130 may change the operating parameters of the device 100 automatically. For example, the control console 130 may change the operating parameters according to a predetermined set of operating steps associated with a procedure. Alternatively, or additionally, the control console 130 may change the operating parameters of the device 100 based on feedback from the device 100 itself. For example, the control console 130 may change the operating parameters of the device 100 in response to a detection of a device resistance, a pressure, a pressure change, a temperature, a temperature change, a determined depth of cut, or the like, during use.

FIG. 1B illustrates a cross-sectional view of the device 100. In the embodiment shown, a height of the proximal end of the suction cup 105 is greater than a height of a distal end of the suction cup 105, forming a tapered circumferential suction chamber 150 in the suction cup 105. The tapered circumferential suction chamber 150 helps ensure even suction is applied, in part, because the height of the chamber decreases as the volume to be evacuated reduces.

In some embodiments, a first height of the tapered circumferential suction chamber 150 may have a first height at an orifice of the suction cup 105 and a second height at an antipodal point of the suction cup. In these embodiments, the first height may be larger than the second height. For example, the height of the suction cup 105 may be greatest at the proximal end and shortest at the distal end. In some embodiments, the relative heights of the proximal end of the suction cup 105 and the distal end of the suction cup 105 may be based on a number of factors, including, but not limited to: the amount of total volume to be evacuated, the amount of suction being applied, the type of procedure being performed, the type of tissue being excised, the amount of electrical energy being applied, features included on the underside of the suction cup 105 (e.g., standoffs and/or visual guides), or the like. For example, the tapered circumferential suction chamber 150 may slope at an angle so that the volume to be removed from the suction cup is proportional to the volume of the tapered circumferential suction chamber 150 along a horizontal axis of the suction cup 105. Examples of the slope angle include, but are not limited, 0 degrees, 1 degree, 2 degrees, 3 degrees, 4 degrees, 5 degrees, 6 degrees, 7 degrees, 8 degrees, 9 degrees, 10 degrees, 11 degrees, 12 degrees, 13 degrees, 14 degrees, or 15 degrees.

Figure 3A:
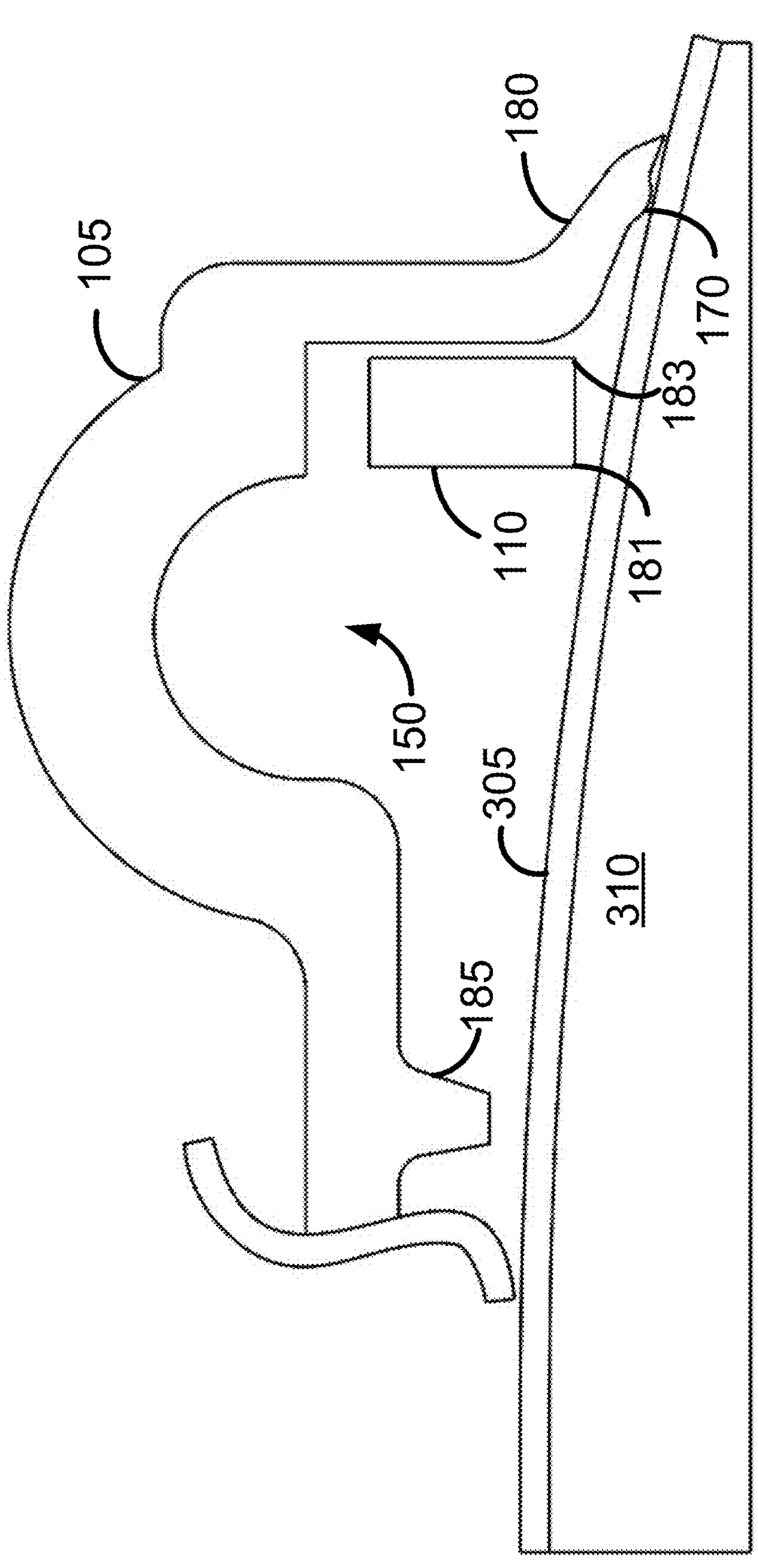
FIG. 3A-3F illustrate steps for using the device shown in FIG. 1A, according to one embodiment.

In addition, the geometry and specifications of the suction cup 105 may be modified to prevent collapse of the suction cup 105 when suction is applied. For example, the top of the tapered circumferential suction chamber 150 may be arched to prevent collapse, as shown in FIG. 3A. The rise and span of the arched portion may vary based on factors including, but not limited to the amount of suction being applied, the type of procedure being performed, or the like.

In addition, the thickness of the suction cup 105 may be modified to prevent collapse when suction is applied. In some embodiments, the thickness of the entire suction cup 105 is a uniform thickness that prevents collapse of the entirety of the suction cup (e.g., 200 microns or more, 175 microns or more, 150 microns or more, 125 microns or more, 100 microns or more, 75 microns or more, 25 microns or more, etc.). In other embodiments, portions of the suction cup may have various thicknesses. For example, portions that should not collapse during use, such as an arched portion of the suction cup 105, may be relatively thicker than other portions of the suction cup 105 that are collapsible during use. In these embodiments, the portions that have an increased thickness may have a thickness around 200 microns or more. Other portions of the suction cup may have thicknesses around 200 microns or less, such as 175 microns or less, 150 microns or less, 125 microns or less, 100 microns or less, as 75 microns or less, 50 microns or less, 25 microns or less, or the like. By limiting the portions of the suction cup 105 that have increased thicknesses, the total amount of silicon required to manufacture the suction cup 105 is reduced and collapse of the suction cup 105 is prevented. Further, by reducing the amount of silicon, the force needed to insert the suction cup 105 through an incision is reduced.

The stem 125 is coupled to the proximal end of the suction cup 105 via an opening within a tapered side of the suction cup 105. A neck 155 of the stem 125 enables the flow of fluid to and from the stem 125 into the suction cup 105 in a direction substantially perpendicular to the direction of the suction force being applied against the tissue. For example, the angle between the flow of fluid to and from the stem 125 and the direction of the suction force being applied against the tissue may be between 85 degrees and 95 degrees, between 80 degrees and 100 degrees, and the like. The substantially perpendicular flow helps ensure uniform distribution of suction. In alternative embodiments, the neck 155 of the stem 125 may be configured to provide substantially vertical flow. In these embodiments, an additional mechanism may be coupled to the neck 155 of the stem 125 to facilitate horizontal flow of suction and/or fluid to the suction cup 105 from the stem 125.

As previously discussed, the device 100 may include a rigid extender (not shown) that is used to extend the cutting element 110 for insertion of the device 100 through an incision, such as a corneal incision. The end of the rigid extender may include one or more prongs to which the cutting element 110 is coupled. The one or more prongs may prevent substantial decoupling of the rigid extender and cutting element 110 during transport. However, the length of the one or more prongs may necessitate a containment pocket 160 that prevents the one or more prongs from puncturing the suction cup 105.

A basic principle of injection molding in device manufacturing is that the intended molded part must not have features that create significant undercuts and prevent the separation of the two mold halves and retrieval of the molded part. In certain cases, the use of side pins may create the predetermined molded features but involve greater cost and may impart less precision. A horizontal containment pocket may represent a significant undercut and may not be able to be manufactured using standard molding techniques with two mold halves that separate in a vertical direction.

To remove the presence of an undercut created by a horizontal containment pocket, the containment pocket 160 may be collapsible between a vertical position and a horizontal position. In some embodiments, the containment pocket 160 may be collapsible between horizontal and vertical positions because of the flexibility of the material of the containment pocket 160. In alternative embodiments, the containment pocket 160 may be collapsible because of one or more joints, or any other suitable collapsing mechanism. For ease of manufacturing, the containment pocket 160 may be molded in the vertical position. The vertical position of the containment pocket 160 helps ensure the containment pocket is easily released as the two mold halves are pulled in a vertical direction to separate. When the containment pocket 160 is collapsed into the horizontal position, it can accept the end of the rigid extender. In some embodiments, the containment pocket 160 is constrained to lie horizontally during transport. It may remain horizontal as the suction cup 105 and cutting element 110 are elongated via a rigid extender. As the rigid extender is retracted, the containment pocket 160 returns to its vertical as molded shape due to silicone's elasticity.

FIG. 1C illustrates an additional cross-sectional view of the device 100. As discussed with reference to FIG. 1B, the suction cup 105 may form a tapered circumferential suction chamber 150 that slopes downward in a direction from the proximal end to the distal end of the suction cup 105. In addition, a central portion 165 of the suction cup 105 may have a shorter height than the tapered circumferential suction chamber 150 of the suction cup 105. The shortened height of the central portion 165 may reduce the amount of material needs to be evacuated from within the space enclosed by the suction cup 105, which facilitates a more uniform distribution of suction. In some embodiments, the entirety of the central portion 165 may be of uniform height. In alternative embodiments, the central portion 165 may slope at the same angle as the tapered circumferential suction chamber 150 or at a different angle as the tapered circumferential suction chamber 150. In addition, the height (s) of the central portion 165 may vary based on the amount of total volume to be evacuated, the amount of suction being applied, the type of procedure being performed, the type of tissue being excised, the amount of electrical energy being applied, features included on the underside of the suction cup 105 (e.g., standoffs and/or visual guides), or the like.

As illustrated in FIG. 1C, the suction cup 105 includes a sealing contact 170 and a tapered edge 175 along the skirt 180 of the suction cup 105. The compliant skirt 180 enables the sealing contact 170 to remain on the capsular membrane even if a handpiece of the device 100 is rotated or translated by an operator of the device 100. The tapered edge 175 may facilitate the placement of the compliant skirt 180 under the iris, e.g., for procedures involving small pupils. In some embodiments, the tapered edge 175 is where a mold parting line is located. The distance between the tapered edge 175 and the sealing contact 170 may be such that flash from the molding process is not long enough to reach the sealing contact 170. For example, a flash|up to 0.25 mm long will not get between the seal and the capsule and cause a leak.

As further illustrated in FIG. 1C, the proximity of the cutting element 110 to the suction cup 105 may help ensure that only inner bottom edge 181 of the cutting element 110 is in physical contract with the tissue being excised (e.g., a capsular membrane). For example, the cutting element may be coupled to a surface of the suction cup such only the inner bottom edge 181 of the cutting element is in contact with the tissue being excised. In these embodiments, upon application of suction to the suction cup 105, the outer diameter of the cutting element 110 is not in physical contact with the tissue being excised. In these embodiments, the outer diameter of the cutting element 110 affects tissue excision remotely through conduction. For example, the outer diameter of the cutting element 110 may be located at a sufficient distance from the capsular membrane to remotely affect the capsular membrane by a temperature change. The temperature change may assist in the creation of a consistent rolled edge, discussed below with reference to FIGS. 3A-3F. In other embodiments, the coupling of the cutting element 110 and suction cup 105 may be configured such that the outer bottom edge 183 of the cutting element excises the tissue, both the inner bottom edge 181 and outer bottom edge 183 excise the tissue, or any other suitable portion of the cutting element 110 excises the tissue.

FIGS. 1D-1F illustrate additional views of the device 100. As shown in FIG. 1D, the cutting element 110 and electrical leads 120A, 120B are installed. In some embodiments, the electrical leads are electrically insulated silver wires (e.g., 6-micron thick layer of polyimide). In some embodiments, the electrical leads 120A, 120B are pushed back near the top of the interior flow chamber to be out of the way of the cutting edge (e.g., the inner bottom edge 181) of the cutting element 110.

The suction cup 105 shown includes one or more features. Features shown may include hollow standoffs, such as hollow standoff 185, and aiming guides, such as aiming guide 190. In the embodiment shown, the hollow standoffs are placed on an inner surface of the suction cup 105. The hollow standoffs prevent the central portion 165 of the suction cup 105 from completely sealing against the capsular membrane surface, creating channels for material flow and a uniform distribution of suction. In addition, the hollow standoffs may provide a visual indication of the suction level within the suction cup 105. As suction develops, the trapped air bubble is removed from the inside of the hollow standoff. The escape of the air bubble can be used as a visual signal that adequate suction has been developed. The dimensions of the standoffs and aiming guides be varied to select one that traps air bubbles and allows escape only when the predetermined level of suction has been applied. In some embodiments, the dimensions of the standoffs may vary such that they provide a visual indication of different levels of suction.

In the embodiment shown, the suction cup 105 includes ten stand-offs. In alternative embodiments, the suction cup 105 may include any suitable number of standoffs, such as one standoff, five standoffs, or the like. In some embodiments, the standoffs have a high aspect ratio air traps (e.g., 0.2 mm diameter and 0.3 mm height). In alternative embodiments, the standoffs have low aspect ratio air traps, intermediate aspect ratio air traps, and the like. Further, the aspect ratio can be modified to ensure that air is always trapped. Because silicone rubber is stretchable, the standoff opening can have a smaller diameter than the trap cavity and still be moldable. Reduced diameter at the opening of the standoff may help ensure that air will be trapped until suction reaches the pressure needed for a successful capsulotomy. However, the diameter of the cavity may include smaller and/or equal dimensions as the standoff opening.

In some embodiments, the standoffs include a slot, e.g., slot 195. The slots face away from the stem 125 and/or suction tubes 115. In alternative embodiments, the slots may face the stem and/or suction tubes 115, each slot may face a different direction, or the like. The slots may be modified to let air out at different levels of suction.

The placement of the capsulotomy at a precise location on the surface of the lens is critical as off-centered capsulotomies may provide less IOL stability and poorer IOL optical performance. The operator may use a number of different surgical landmarks to center the capsulotomy. These include the positions of certain Purkinje images or light reflections that may be used to indicate the position of the patient's visual axis. An automated capsulotomy device, such as device 100 should allow easy centration of the cutting element 110 aligned with such Purkinje images. In the device 100 shown, the alignment of the center of the suction cup 105 with a predetermined surgical landmark such as a Purkinje light reflection is assisted by the placement of aiming guides, such aiming guide 190, near the center of the suction cup 105. Aiming guides may have various geometric shapes and assist in the operator's visual recognition of the location of the center of the suction cup 105 and/or the cutting element 110. Aiming guides may be manufactured onto the suction cup 105 using silicone micro-molding techniques that are well known in the art.

Once the predetermined alignment of the suction cup 105 has been identified, the initiation of suction must not cause a substantial shift in the position of the cutting element 110, which may result in an off-centered capsulotomy. Undesirable movement of the cutting element 110 can occur if the cutting element 110 is merely inserted into holes in the suction cup 105 that do not completely constrain cutting element 110 movements as the suction cup 105 reduces its internal volume under suction. To prevent undesirable movement, the cutting element 110 may be physically bonded to the suction cup 105, as shown in FIG. 1E.

The cutting element 110 consists of a conductive metal and the suction cup 105 may consist of silicone and thus are made as two separate parts. Hollow pockets, such as pocket 197 are disposed in the suction cup 105 to accept one or more tabs protruding from the cutting element 110. During manufacture, the tabs are placed within the corresponding hollow pockets and silicone is deposited into the hollow pockets to secure the attachment tabs in place. In some embodiments, the silicone is potted from the topside of the suction cup 105. In alternative embodiments, the silicone is potted from the bottom side of the suction cup 105. For example, during bottom potting, liquid silicone may be dispensed in each pocket. The cutting element 110 is then brought to the suction cup 105, the electrical leads 120A, 120B are fed through the lumen of the stem 125, and the attachment tabs are submerged in the liquid silicone in the potting pockets. The assembly may then be heated to cure the silicone. In some embodiments, the pockets include a thin membrane that prevents the liquid silicone from getting onto the cutting element 110. The thin membrane may be pierced by the attachment tabs as the attachment tabs are placed into the hollow pockets.

Figure 2:
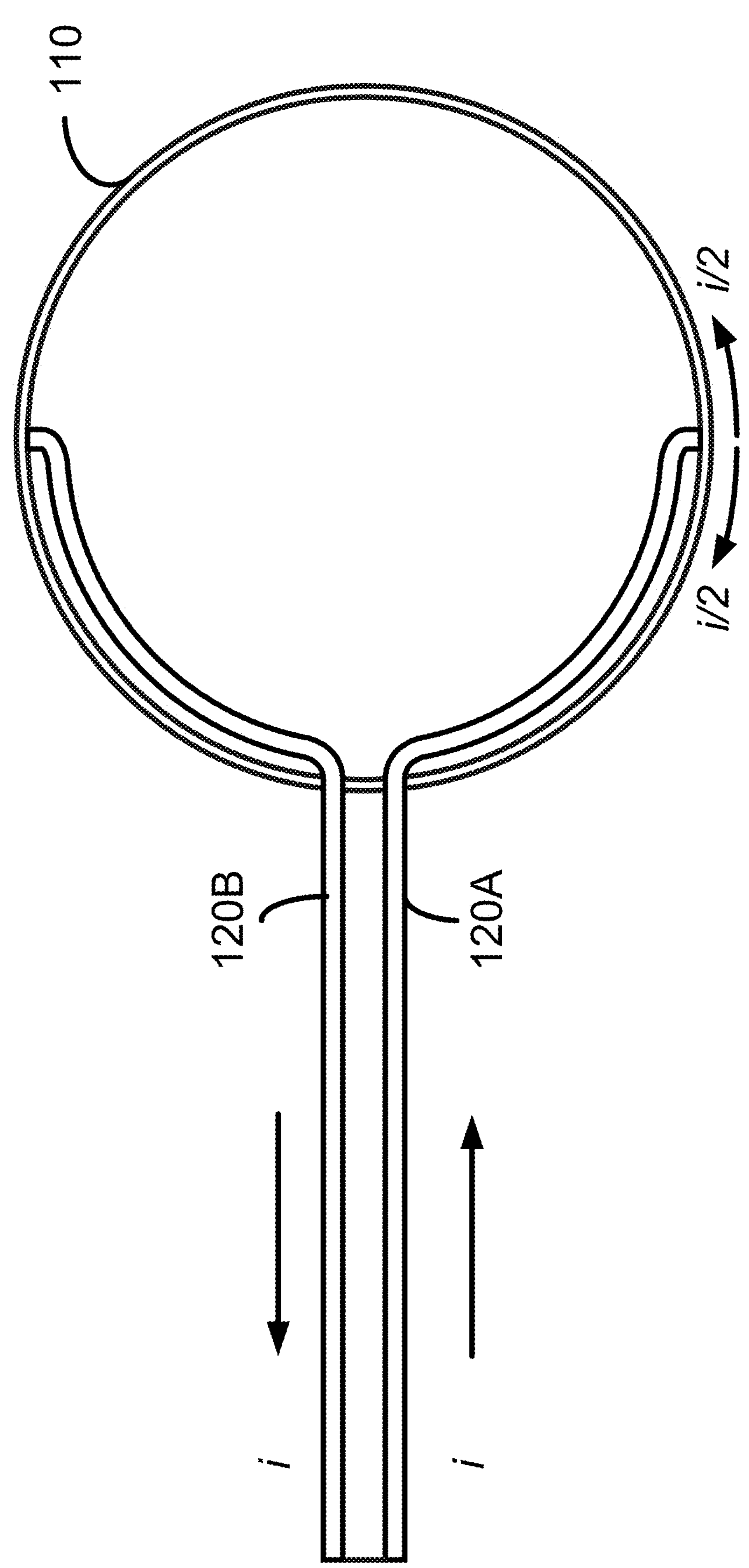
FIG. 2 illustrates the flow of current through the cutting element of the microsurgical device shown in FIG. 1A, according to one embodiment.

FIG. 2 illustrates the path of electrical current flow (i) within the cutting element 110. Upon entering the cutting element 110 through an electrical lead 120A, a portion of the current, such as one half of the current ($i_{1/2}$), travels along one half of the cutting element 110, while another portion of the current, such as the other half of the current ($i_{1/2}$), travels along the other half of the cutting element 110. Current then exits the cutting element 110 at the other electrical lead 120B. Due to the electrical resistance of the cutting element 110, the current flow causes a rapid increase in the temperature of the cutting element 110. Because of the rapid increase in temperature, the water molecules near or adjacent to the cutting element 110 and the tissue being excised vaporize rapidly and mechanically fracture the tissue along the path dictated by the portion of tissue being excised.

FIG. 3A-3F illustrate steps for using the device 100 shown in FIG. 1A, according to one embodiment. FIG. 3A a cross-section of the device 100 in close proximity to the capsular membrane 305 that encloses the lens capsule 310. In the cross-section shown, the suction cup 105 has a flow channel where the silicone is arched and thick enough to prevent collapse when the suction is applied, e.g., along tapered circumferential suction chamber 150 of the suction cup 105. The standoffs, such as standoff 185, keep the flow path under the center of the membrane open during suction. The body of the cutting element 110 illustrated has a rectangular cross-section. In alternative embodiments, the cutting element 110 may be any suitable shape, such as conical, elliptical, and the like.

The sealing contact 170 of the skirt 180 of the suction cup 105 comes into close proximity to the capsular membrane 305 which encloses the lens 310. An operator of the device centers the device 100 on the patient's visual axis. Once centered, the rigid extender has been retracted from its extended position such that the end of the rigid extender is in the neck 155 of the device 100. The rigidity of the rigid extender enables the operator to position the suction cup 105 on the visual axis over a large range of anterior chamber depth, ACD, (e.g., ACD 1.9 mm to 4.0 mm).

Figure 3B:
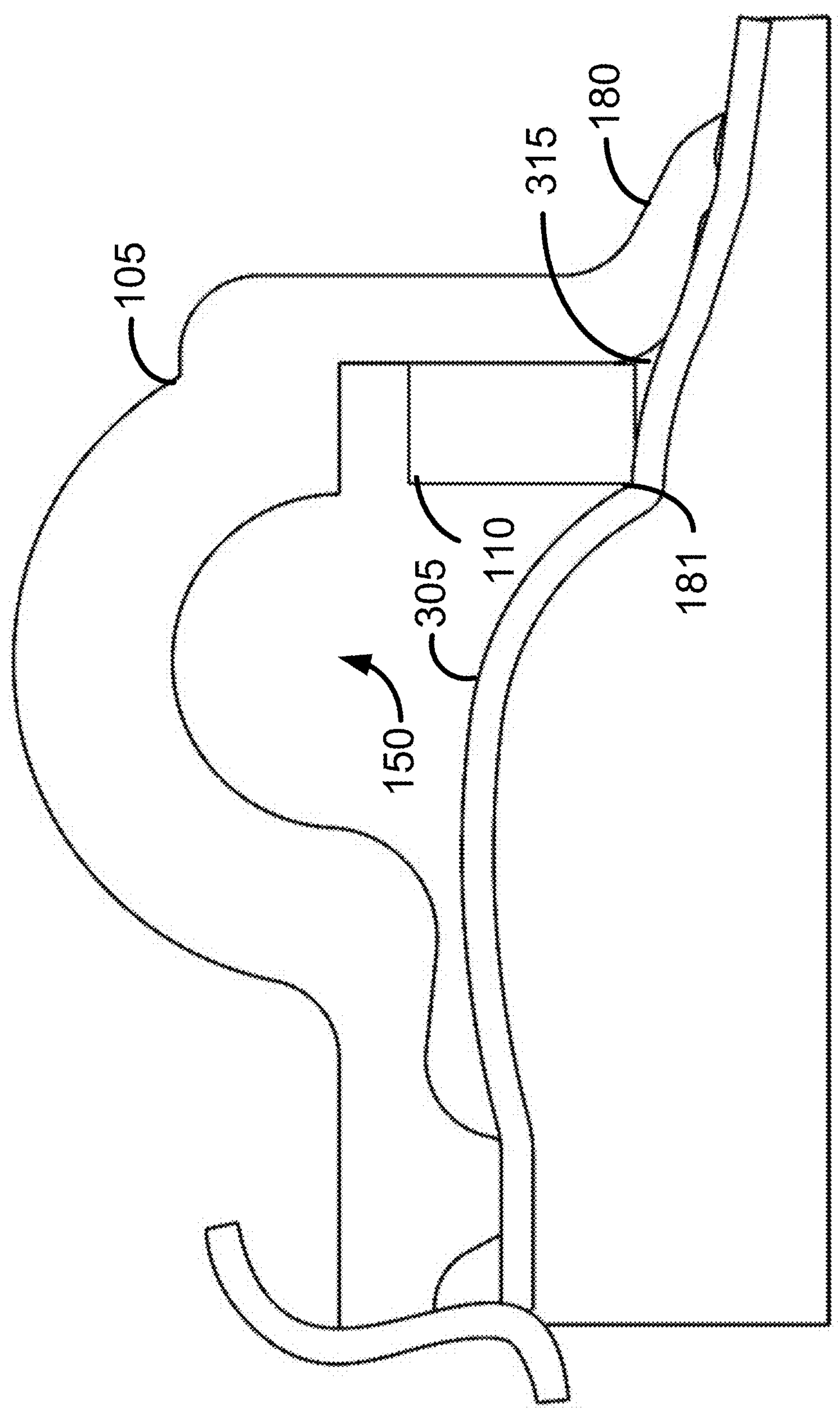

FIG. 3B illustrates the deformation of the lens 310 and suction cup 105 that occur when suction is applied to the suction cup 105. The suction forces pull the capsular membrane 305 inside the suction cup 105 and establish a contact force against the inner bottom edge 181 of the cutting element 110. Concurrently, a surface of the suction cup 105 is pulled against the outer surface of the cutting element 110. The skirt 180 of the suction cup 105 prevents contact between the capsular membrane and the outer bottom edge 183 of the cutting element 110 to limit cutting to the inner bottom edge 181 of the cutting element 110. In alternative embodiments, cutting may occur at the outer bottom edge 183 of the cutting element 110, at both the inner bottom edge 181 and outer bottom edge 183 of the cutting element 110, or the like.

A small volume 315 is created such that liquid there is trapped between the capsular membrane 305, cutting element 110, and suction cup 105. The stretching force from suction causes capsular membrane 305 to develop significant tensile stress. There is a tensile stress concentration where the capsular membrane 305 is in contact with the inner bottom edge 181 of the cutting element 110. Since this tensile stress is built up prior to the electrical discharge that makes the cut, it is already there waiting to act at the instant that the discharge occurs, and a brief flash of heat is added. In some embodiments, small volume 315 separating the outer diameter of the cutting element 110 and the capsular membrane 305 is sufficiently small that it allows the cutting element 110 to remotely cause a temperature change in the capsular membrane 305 from a distance to aid in the capsular roll up after the cutting procedure is complete.

Figure 3C:
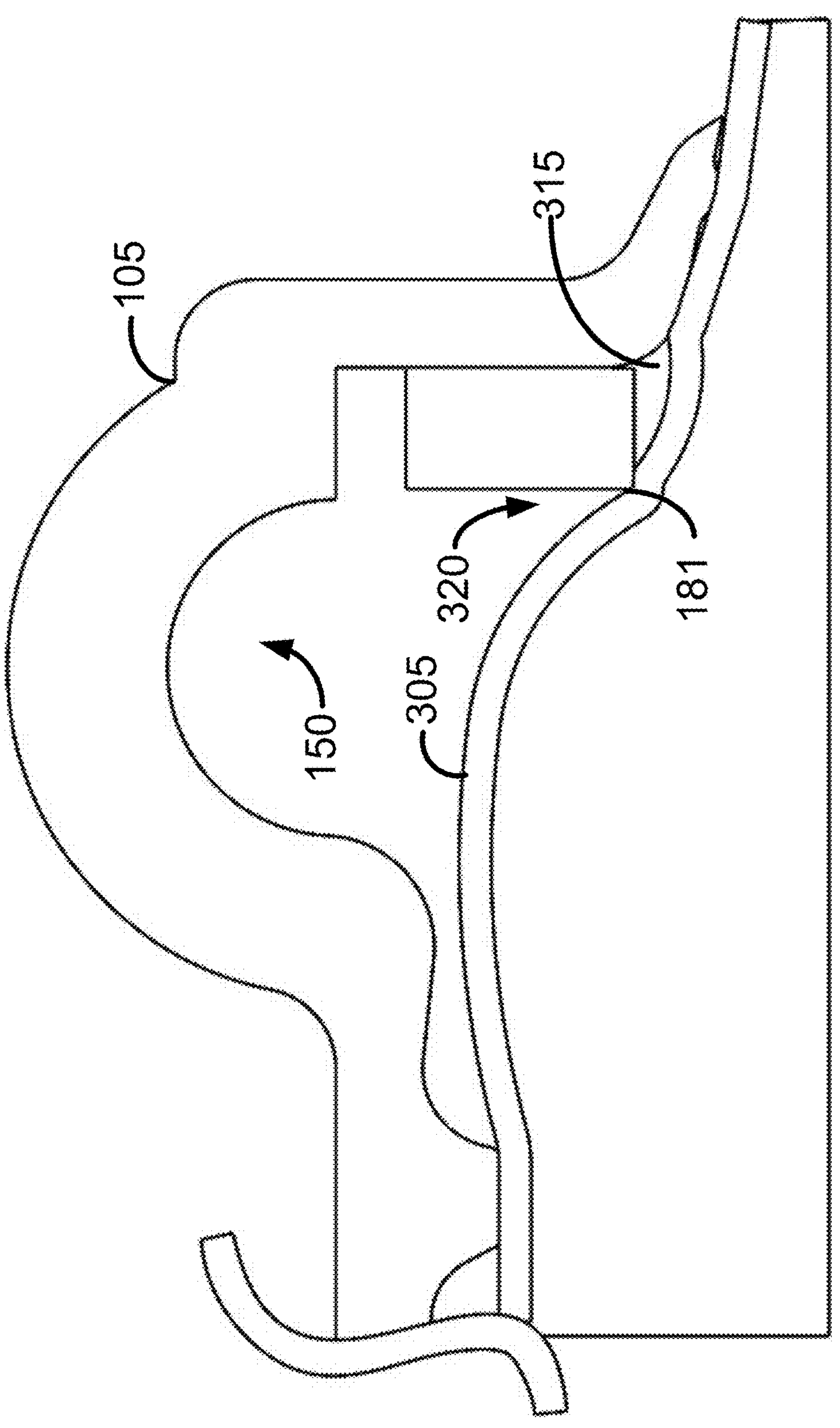

FIG. 3C illustrates the condition when the electrical discharge is occurring through the cutting element 110. Within the first few microseconds of the cutting event, the cutting element 110 heats up to a temperature hotter than the critical temperature of water. As a result, the water molecules located within a few microns of the cutting element 110 vaporize. The steam within the trapped small volume 315 cannot escape during this short time, so the pressure in the trapped small volume 315 rises. The increase in pressure results in the change of curvature that appears in the capsular membrane 305. This may also cause a change in volume of the small volume 315.

At the same time, heat is flowing from the cutting element 110 into the capsular membrane 305 at the point of contact with the cutting element 110 (e.g., the inner bottom edge 181 of the cutting element 110). As heat flows into the collagen at the point of contact between the capsular membrane 305 and the cutting element 110, the capsular membrane 305 weakens. Due to the symmetry of the device 100, equal forces and temperatures are exerted across the circumference of the cutting element 110 in contact with the capsular membrane 305. When the strength of the capsular membrane 305 is less than the forces acting to tear it, the capsular membrane 305 breaks. The forces acting to tear the capsular membrane 305 may arise from 1) the tensile stress from the suction being applied, and/or 2) the increasing pressure in the small volume 315 as a result of the steam heating up.

Because the cutting event, occurs on the millisecond time scale (e.g., 1 millisecond to 10 milliseconds), it is the inertia of the surrounding mass of material that confines the steam. It would take a great force to accelerate the surrounding mass of material during this brief time interval. During the millisecond time interval, the steam pressure builds, the material will start to move, but the capsulotomy is done by then. For example, the electrical discharge may consist of 12 pulses, 66 microseconds on, 305 microseconds off, for a total time of 4 milliseconds. This may not be enough time for the mass of material to accelerate and move. Note that the cutting of different thickness capsules or other tissues may be performed by altering the number of pulses, duration of each pulse, interpulse interval, and energy per pulse. In addition, the width of the bottom aspect of the cutting ring may be adjusted to change the spatial extent of remote temperature effects such as the roll up.

Figure 3D:
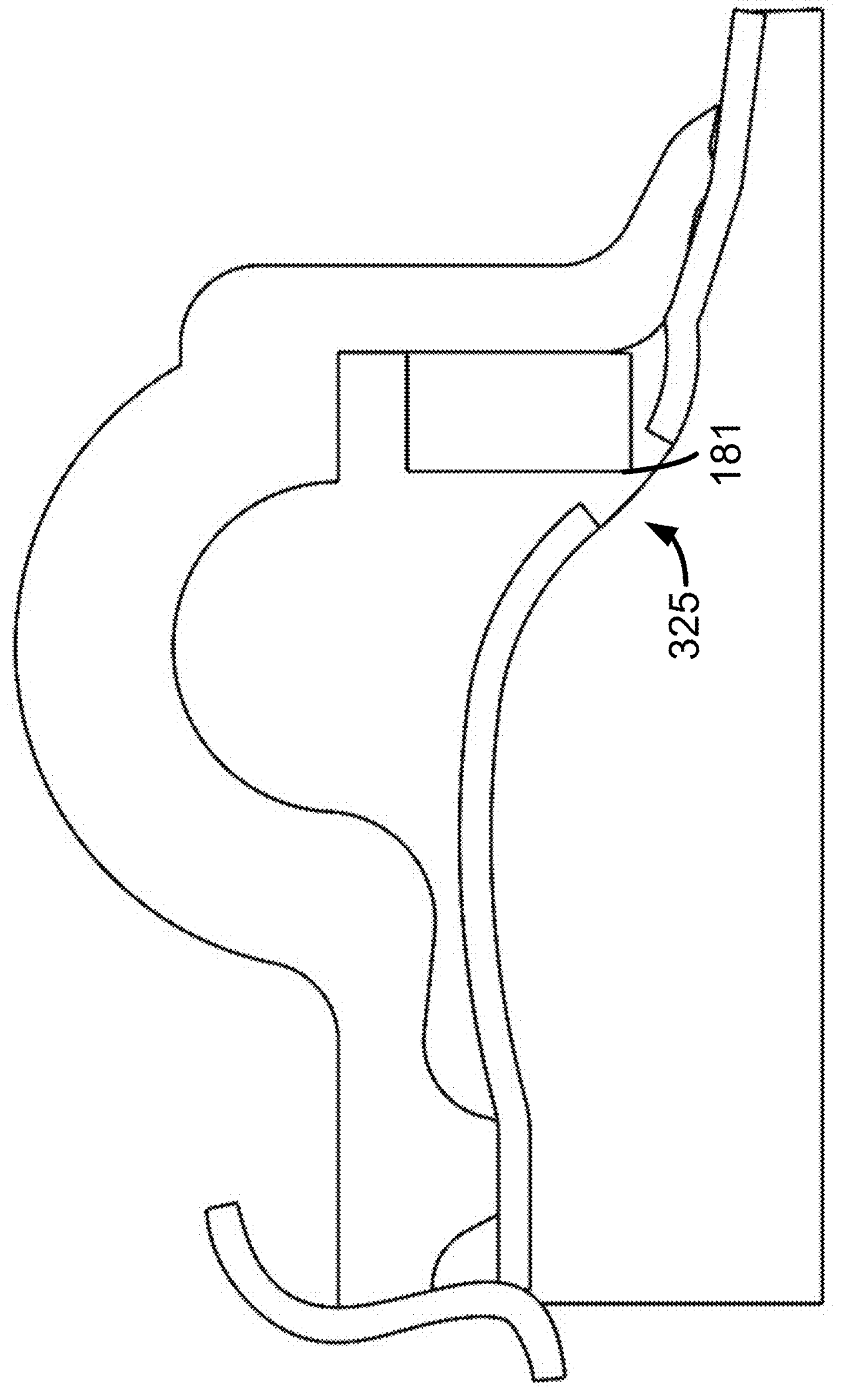

FIG. 3D illustrates the pullback 325 of the stretched capsular membrane 305 from the inner bottom edge 181 of the cutting element 110, which occurs after the electrical discharge has completed. In some embodiments, there is little inertial mass involved in this movement.

Figure 3E:
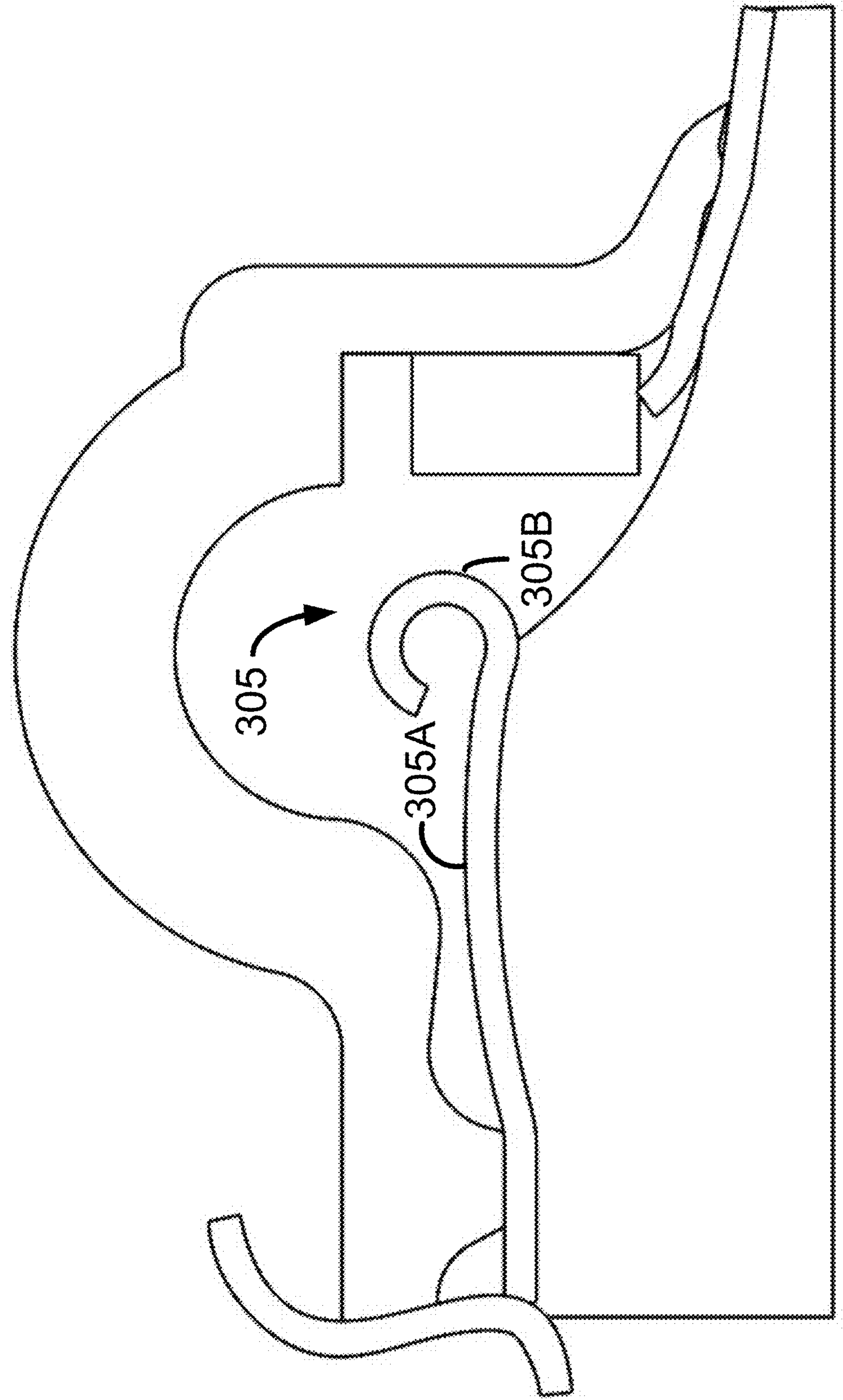

FIG. 3E illustrates the edges of the capsular membrane 305 roll up as edges cool. The edges of the capsular membrane 305 roll up because the heating method employed by the device 100 creates a temperature gradient through the thickness of the capsular membrane 305. As discussed with respect to FIG. 3B, the outer surface of the capsular membrane 305 will receive heat from the cutting element 110 through the steam that contacts it, such as the steam confined within the small volume 315. The heat causes the collagen to shrink. The collagen shrinks more at the outer surface 305A of the capsular membrane 305 than at the inner surface 305B of the capsular membrane 305 because the cutting event is too brief for significant heat to get through the steam layer and shrink the inner surface 305B of the capsular membrane 305 as much the outer surface 305A. This creates a tensile stress gradient through the thickness of the capsular membrane 305 as it cools down. The shrinkage of the collagen in the top layer pulls the edge in so it rolls up. The edge of the capsular bag can only roll up until it contacts the bottom of the cutting element 110 and/or the suction cup 105.

Figure 3F:
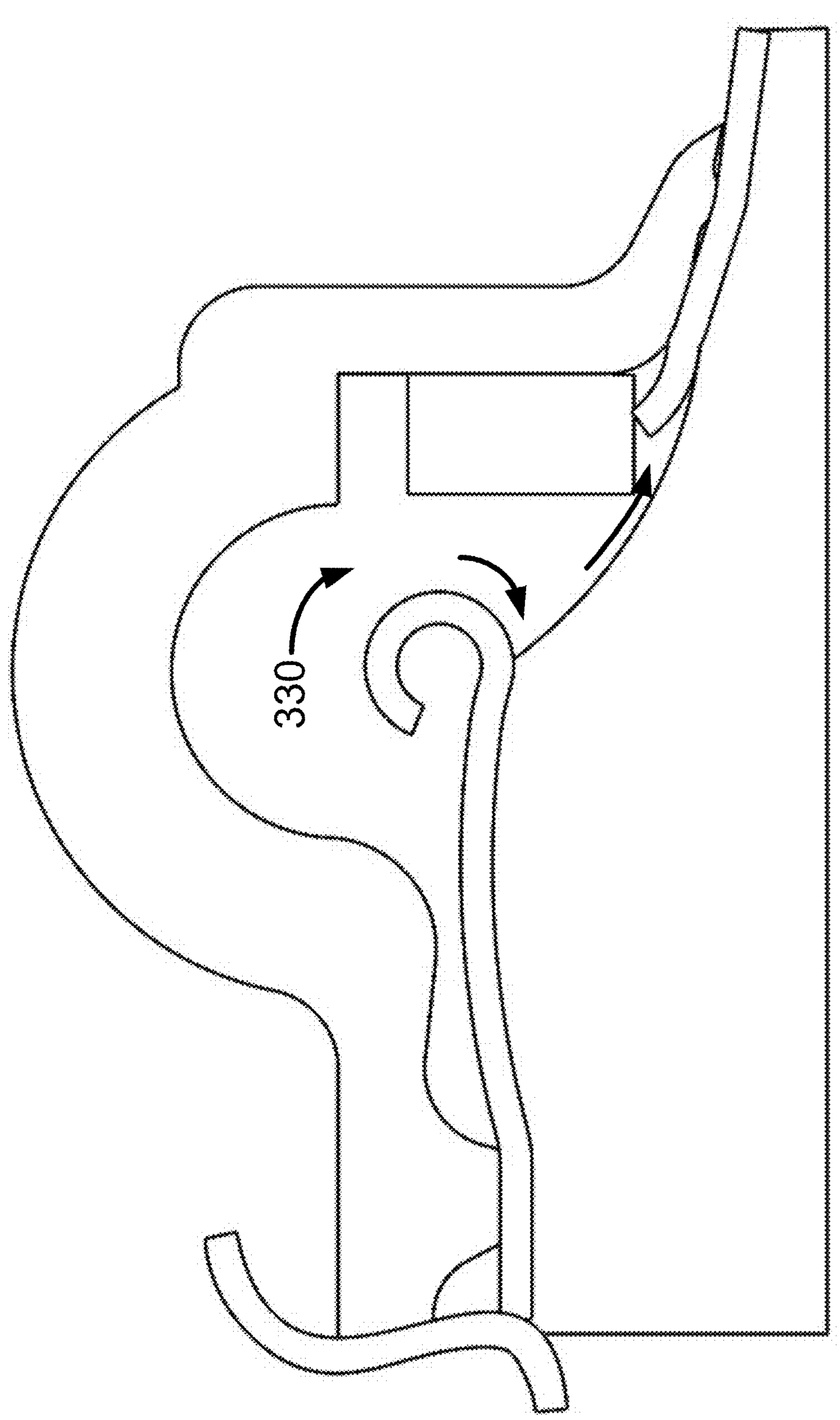

FIG. 3F illustrates the flow direction 330 of the fluid release that is performed to disengage suction and lift the suction cup 105 off the lens 310. Because the edge of the capsular bag is rolled up against the bottom of the cutting element 110 and suction cup 105, the flow at that location goes between the capsular membrane 305 and the lens 310. This performs a hydrodissection to separate capsular membrane 305 from the lens 310.

As the fluid release progresses, the edge of the capsular bag is still rolled up against the bottom of the suction cup 105, so fluid is still being directed between the capsular membrane 305 and the lens 310 to complete the hydrodissection. In some embodiments, the fluid release is performed rapidly (e.g., 0.5 seconds or less). If the release flow is fast enough, inertia of the surrounding fluid above the suction cup 105 may delay it rising long enough for the release flow to follow the path of the hydrodissection rather than simply floating off the suction cup 105. Once the edge of the capsule bag is no longer held down by the suction cup 105, the capsular bag is free to roll up under the influence of the surface stress induced by the flash of heat that came to it during the cutting event.

Superelastic Nitinol Ring

Figure 4A:
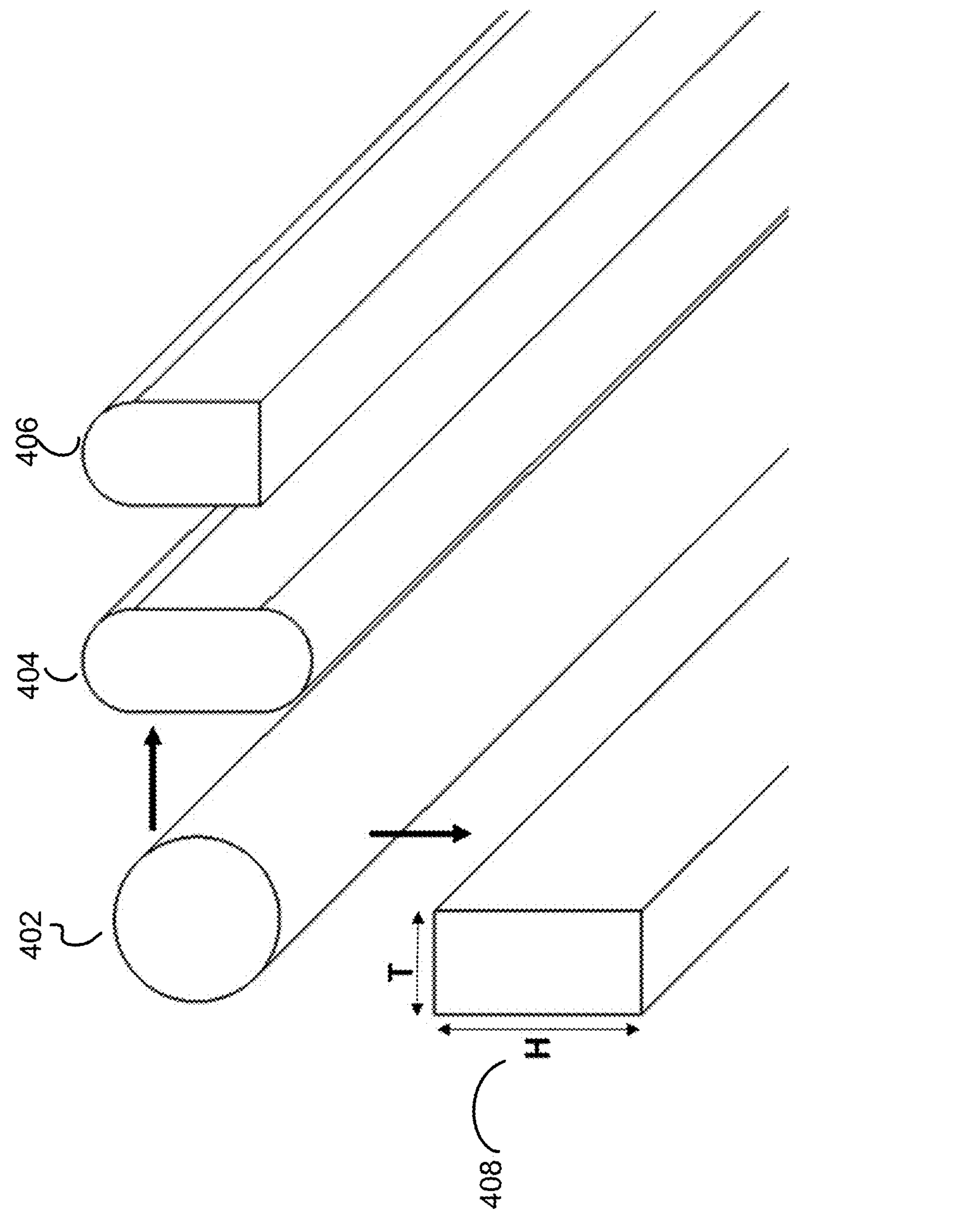
FIG. 4A shows cross sections of example nitinol wires, according to one embodiment.

FIG. 4A shows cross sections of example nitinol wires. Nitinol wires may be processed to achieve a predetermined size and shape. As shown in FIG. 4A, the wire may be pre-processed to have a circular cross section, e.g., wire 402. For example, nitinol wires with a circular cross section may be manufactured to have a predetermined diameter with a tight tolerance (e.g., +/−0.0001 inch). For instance, a circular wire may have little variation in current carrying cross sectional area over the length needed for one ring (e.g., 13.82 mm). In some embodiments, a super elastic ring may be made of the nitinol wire with a circular cross section. Round wires may be welded together to form a high aspect ratio structure that may be used to form a ring with adequate stiffness perpendicular to the plane of the ring (i.e. perpendicular to its circular footprint). The round wires may be used directly, using electrical resistance welding to weld the wires together along their length to make a ribbon (e.g., a form of "seam welding"). Tabs and electrical lead stubs may be welded on. The ribbon may be cut into segments of the proper length and the ends welded together to make a ring.

Alternatively, the nitinol wire with a circular cross section may run through rollers to plastically deform the wire into a rectangular cross section. The process of rolling the round wire to flat wire may introduce a tolerance on the wire height (H) and wire thickness (T) in such a way that the cross-sectional area of the wire remains the same. For example, when the circular wire is rolled flat, any variation in thickness T will be compensated for by an equal area variation of opposite sign in height H. In this way, the cross-sectional area of the nitinol wire stays constant, thus allowing uniformity in the ring heating. In one implementation, the nitinol wire with a circular cross section may be compressed on two opposite sides of the nitinol wire to produce permanently flattened edges on both sides, e.g., wire 404 in FIG. 4A. The flattened wire may be of at least a threshold thickness T. The flattened wire may be further manufactured to make different shaped edges as predetermined. In one example, the flattened wire may be further processed to have a rectangular cross section. As shown in FIG. 4A, the wire 406 has two opposite sides (first side and second side) flattened. A third side of the wire 406 is processed by cutting/grinding a portion of the third side. A rectangular cross section wire 408 may be obtained by cutting/grinding a fourth side, opposite to the third side of the wire 406. The rectangular cross section may have a height (H) and a thickness (T). In some embodiments, wire 408 may be of at least a threshold height (H). In some embodiments, the wire 408 may be further processed with a precision grinding on the 4 sides of the wire 408 so that the final dimensions (H and T) may have an even tighter tolerance. In some embodiments, lapping may be performed to the wire to produce a sharper corner at the edge. The lapping may be performed after the ring is welded together and all tabs and lead stub welding are completed. Alternatively, grinding and/or lapping may be performed prior to attaching the tabs to the ring.

Figure 4B:
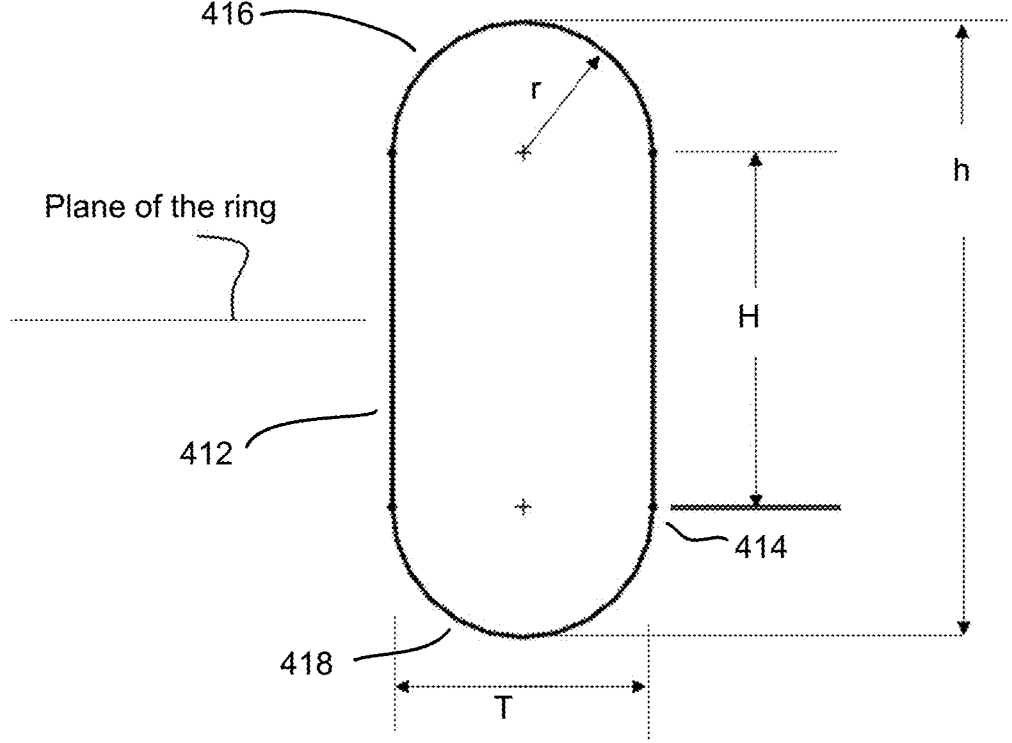
FIG. 4B shows an example wire with a flattened cross section, according to one embodiment.

FIG. 4B shows an example wire with a flattened cross section. The nitinol wire may initially have a diameter of 0.00455+/−0.0001 inch (0.116+/−0.008 mm). The tolerance on the variation of the diameter along the length of the wire is a critical dimension. In some embodiments, within any continuous one inch of length along the wire, the change in diameter is no more than +/−0.0001 inch. The circular wire may be flattened to have a cross section as shown in FIG. 4B. In this example, the wire is compressed on the first side 412 and the second side 414. The two compressed sides 412 and 414 are connected by a half circle 416 or 418, on each end. The two half circles 416 and 418 may each form a third side and a fourth side of the wire, respectively. The radius (r) of the half circle 416/418 may be 0.035 mm, the height of the wire (H) may be 0.095+/−0.009 mm, and the thickness of the wire (T) may be 0.070+/−0.009 mm. In some embodiments, the thickness of the wire may be the same as the ring thickness. A ring height (h) may refer to the distance between the third side and fourth side of the wire. In some implementations, the aspect ratio of a ring (ring height/ring thickness) may be 1.5 or more (e.g., the ring height is at least 1.5 times greater than the ring thickness) so that the ring may be bend easily in-plane and be stable against out-of-plane bending.

Figure 5:
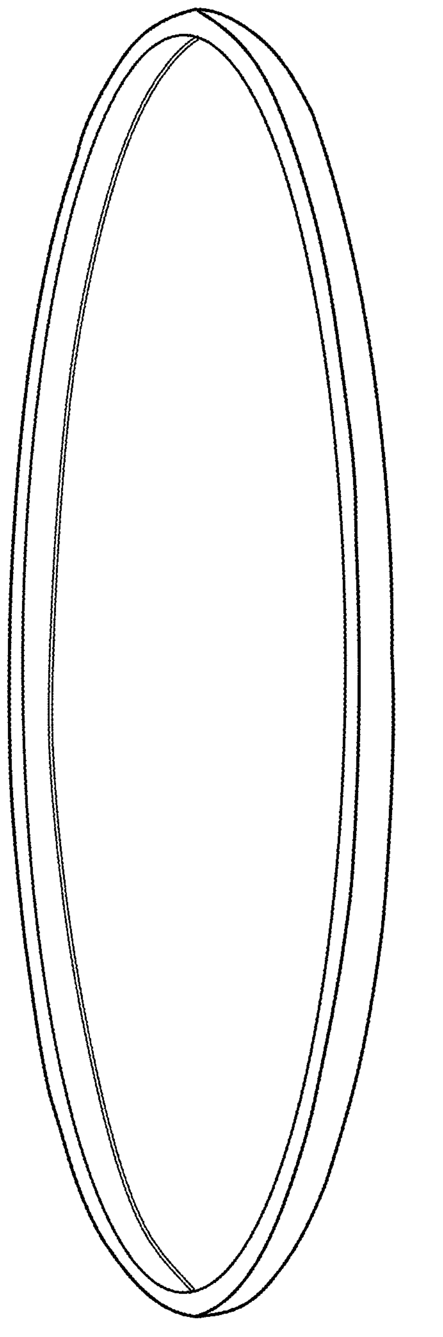
FIG. 5 shows an example of super elastic nitinol ring, according to one embodiment.

In some implementations, after the wire is processed to have a cross section of a predetermined shape and size, the wire may be cut to a predetermined length (e.g., 13.82 mm) and bent into a circle, i.e., connecting two ends of the wire. The two ends of the wire may be welded together to form a closed ring. In one implementation, the welding point (e.g., the point where the two ends of the wire connect) is grinded to obtain a smooth seam to match the neighboring wire surface. In some implementations, the mechanical work, such as compressing, cutting, grinding, bending, welding, etc., is performed at the martensitic state of the nitinol wire, because it is an easily deformable non-super-elastic state. After all mechanical work is completed, the finished structure may be annealed at a predetermined temperature (e.g., ranging from about 450° C. to 650° C.) to make the nitinol wire austenitic, thus becoming super elastic. FIG. 5 shows an example of super elastic nitinol ring. The ring may have an outer diameter (OD) of 4.4+/−0.025 mm.

In some embodiments, the super elastic nitinol ring may be prepared from a sheet material. For example, a nitinol material is processed (e.g., flattened) to generate a sheet with a uniform thickness in the martensitic state. The nitinol sheet may be cut into a plurality of strips, and each nitinol strip may have a rectangular cross section. The rectangular cross section may have a height (H) and a thickness (T). In some embodiments, the nitinol strip may be further processed with a precision grinding on the four sides of the nitinol strip so that the final dimensions (H and T) may reach desired values with a tight tolerance. In some embodiments, lapping may be performed to the nitinol strip to produce a sharper corner at the edge. The nitinol strip may be cut to a predetermined length (e.g., 13.82 mm) and bent into a ring shape such that the two ends of the nitinol strip are aligned and coupled to produce a nitinol ring. The two ends of the nitinol strip may be welded together to permanently form a closed ring. In one implementation, the welding point (e.g., the point where the two ends of the wire connect) is grinded to obtain a smooth seam to match the neighboring wire surface. In some implementations, the nitinol ring may be annealed at a predetermined temperature (e.g., ranging from about 450° C. to 650° C.) to make the nitinol strip austenitic, thus becoming super elastic.

Figure 6:
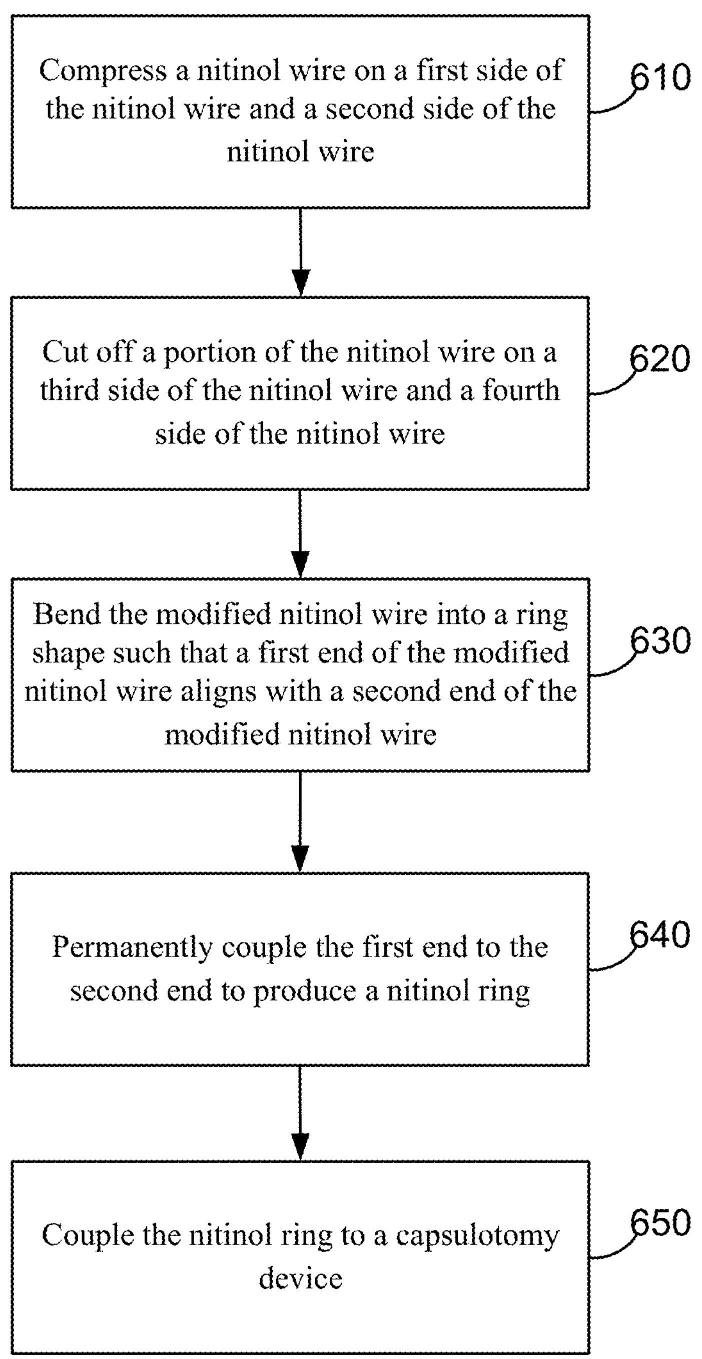
FIG. 6 is an example method for manufacturing a super elastic nitinol ring for cataract capsulotomy, according to one embodiment.

FIG. 6 shows an example method for manufacturing a super elastic nitinol ring for cataract capsulotomy. Embodiments may include different and/or additional steps, or perform the steps in different orders. In some embodiments, the method may include compressing 610 a nitinol wire on a first side of the nitinol wire and a second side of the nitinol wire. The nitinol wire may include a circular cross section. The first side may be an opposite side of the second side of the nitinol wire. The nitinol wire may be compressed to produce permanently flattened edges on the first side and the second side of the nitinol wire. In some implementations, the compressed nitinol wire may have at least a threshold width/thickness between the edges on the first side and the second side. For example, the width of the compressed wire may be 0.070+/−0.009 mm.

The method may include cutting off 620 a portion of the nitinol wire on a third side of the nitinol wire and a fourth side of the nitinol wire. The fourth side is opposite to the third side. In this way, a modified nitinol wire may be produced to have flattened edges on the third side and the fourth side, and the modified nitinol wire may include at least a threshold height. In one example, the height of the nitinol wire may be 0.095+/−0.009 mm. In some examples, the modified nitinol wire may include a rectangular cross section. The rectangular cross section may be formed by the flattened edges on the first side, second side, third side and fourth side. The cross section of the nitinol ring may be within a threshold range throughout the entirety of the nitinol ring. The cross-sectional area of the nitinol wire may stay constant.

The method may further include bending 630 the modified nitinol wire into a ring shape such that a first end of the modified nitinol wire aligns with a second end of the modified nitinol wire (e.g., at a connection point), and permanently coupling 640 the first end to the second end to produce a nitinol ring. In some implementations, to permanently couple the two ends, the first end and the second end of the wire may be welded together at the connection point (e.g., weld joint) to form a closed ring. The connection point may be filed/grinded to obtain a smooth seam to match the neighboring wire surface. In some implementations, the welding methods may include: electrical resistance welding, laser welding, electron beam welding, percussive welding, ultrasonic friction welding, and diffusion bonding.

The method may further include coupling 650 the nitinol ring to a capsulotomy device. In this way, the nitinol ring, upon receiving current flow from the capsulotomy device, produces heat sufficient to cut tissue in contact with the nitinol ring.

In some embodiments, leads (e.g., nitinol lead stubs) may be permanently coupled to opposite sides of the nitinol ring for carrying electric current. For example, one lead may be coupled to a seam formed at the permanently coupled ends (e.g., the weld joint) of the nitinol ring. In some implementations, the nitinol ring may be coated with copper on one or more sides of the nitinol ring, and in some implementations, one or more tabs may be coupled to a top side of the nitinol ring.

It is not necessary to restrict the embodiments included in the present disclosure to wires with rectangular cross sections. The disclosed method applies to producing wires with any wire-like geometry. For example, square edged "wire" may be produced to tight tolerances by slitting from strips or sheets. Passing low tolerance wire between sets of precision grinding wheels may be used to make tight tolerance wire, and the wheels can have various shaped profiles to create wire with a desired cross-sectional shape (e.g., sharp edge, or filleted edges). In one example, a relatively sharp edge may be on the inner diameter edge of the ring to put high stress on the capsular membrane where cutting is to occur.

Figure 7:
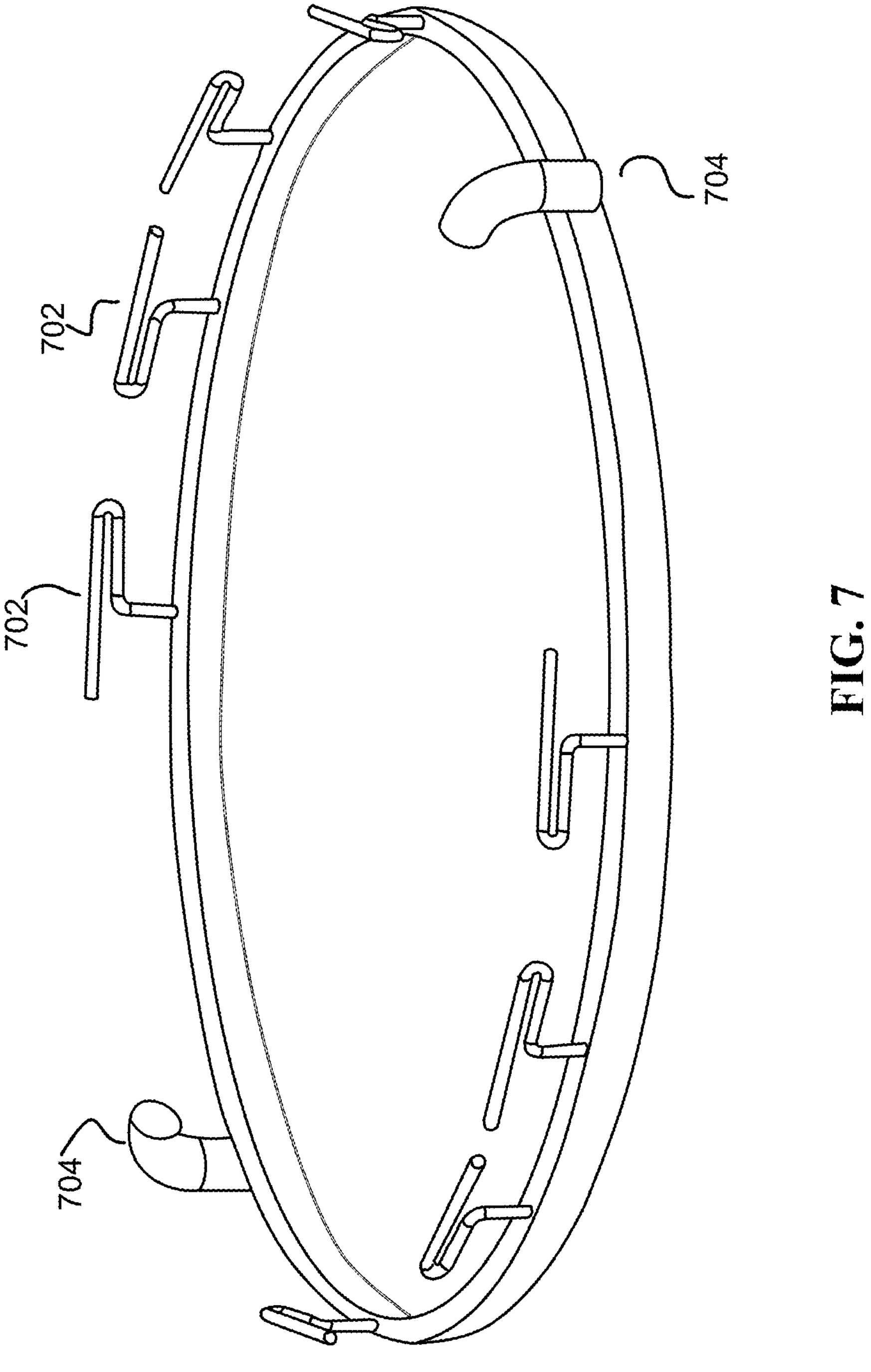
FIG. 7 shows an example super elastic ring used in eye surgery device for cataract surgery, according to one embodiment.

FIG. 7 shows an example super elastic ring used in eye surgery device for cataract surgery. The ring may be coupled with one or more tabs for attachment to a suction cup. The tabs may include various shapes, such as "L" shape, "T" shape, etc. In FIG. 7, one or more short segments 702 are welded on the nitinol ring. In some embodiments, the short segments 702 may include the same nitinol alloy as the nitinol wire. In one example, 8 short segments, each having a diameter of 0.1 mm, may be welded on the nitinol ring. In some examples, one or more nitinol wires 704 may be welded over the butt weld of the nitinol ring, and the nitinol wires 704 may be used as lead stubs for coupling leads. As shown in FIG. 7, two nitinol wires 704 are welded on the nitinol ring, and each nitinol wire 704 may have a diameter of 0.164 mm. In some implementations, the lead stubs may be 180 degrees apart and bring current as near as possible to the bottom of the ring. In one implementation, the nitinol lead stubs have a cross sectional area that gives the same current density as in the nitinol ring so that the nitinol lead stubs will heat up to the same temperature as the ring and prevent the copper wire from sinking heat from the ring during the capsulotomy cutting process. In one example, the ring cross section=0.050 mm×0.225 mm and the lead stubs made from 0.168 mm diameter nitinol wire (flattened at the end where it is welded to the ring), the ring and the lead stubs have the same cross-sectional area.

Figure 8:
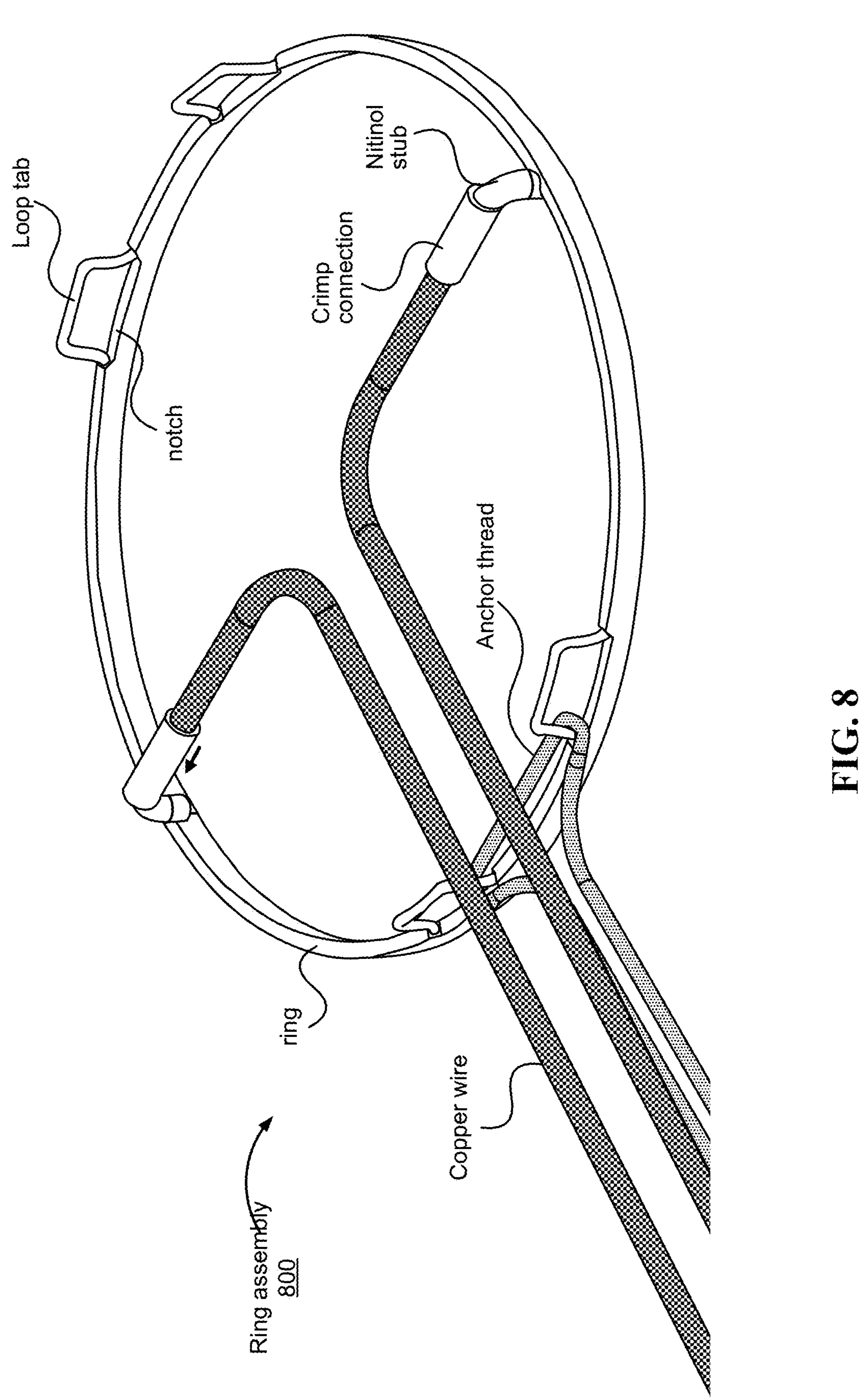
FIG. 8 shows an example wired ring assembly, according to one embodiment.

FIG. 8 shows an example wired ring assembly 800. The ring assembly 800 may include: a super elastic nitinol ring, one or more tabs for attachment to a silicone suction cup, notches to control current density, nitinol lead stubs, ferrules for copper wire attachment, copper wires, and anchor thread for stretching the ring for insertion into the eye. In some implementations, a crimper may be used to deform the ferrules and squeeze the copper wire to insert the copper wire inside the ferrule, the copper wire may have a high compressive contact (crimp connection) with the ferrules which is crimped onto the nitinol lead stubs at the other end. Alternatively, the copper wire could be shaped as a hollow tube at its end to directly crimp onto or be welded to the stub.

In some embodiments, an efficient high-speed process includes feeding long rolls of continuous wire into a welding process, forming tabs at correct locations, and attaching nitinol lead stubs at correct locations. The individual ring lengths are cut, and the lengths are bent to form a ring to bring the two cut ends together and are welded together (a "ring joining weld"). A second nitinol lead stub may be welded over the ring joining weld. Any bumps in the weld may be ground and/or polished off so that the ring surface that contacts the capsule is smooth and continuous. In this way, mechanically there are no discontinuities or offsets that would perturb the capsular membrane cutting process. The super-elasticity, and mechanical strength of the ring joining weld are not a major concern because this is the lowest stress point in the structure (in contrast to the distal and proximal points which undergo the greatest deflection in use). Welding a nitinol (or stainless steel) lead stub over the ring joining weld adds to the strength of the joint.

The formed nitinol ring may be permanently attached to an elastomeric (e.g., silicone, or polyurethane) suction cup by dispensing uncured elastomer over the tabs of the ring, and then polymerizing it to bond the nitinol ring to the suction cup. The potting of the ring tabs may seal all holes so the suction cup does not leak during use. In some embodiments, a top potting method may be used to lock the ring to the suction cup. Silicone may be dispensed to cover the ring tabs. The assembly may be thermally cured to lock the ring to the suction cup to seal against all leaks.

Figure 9:
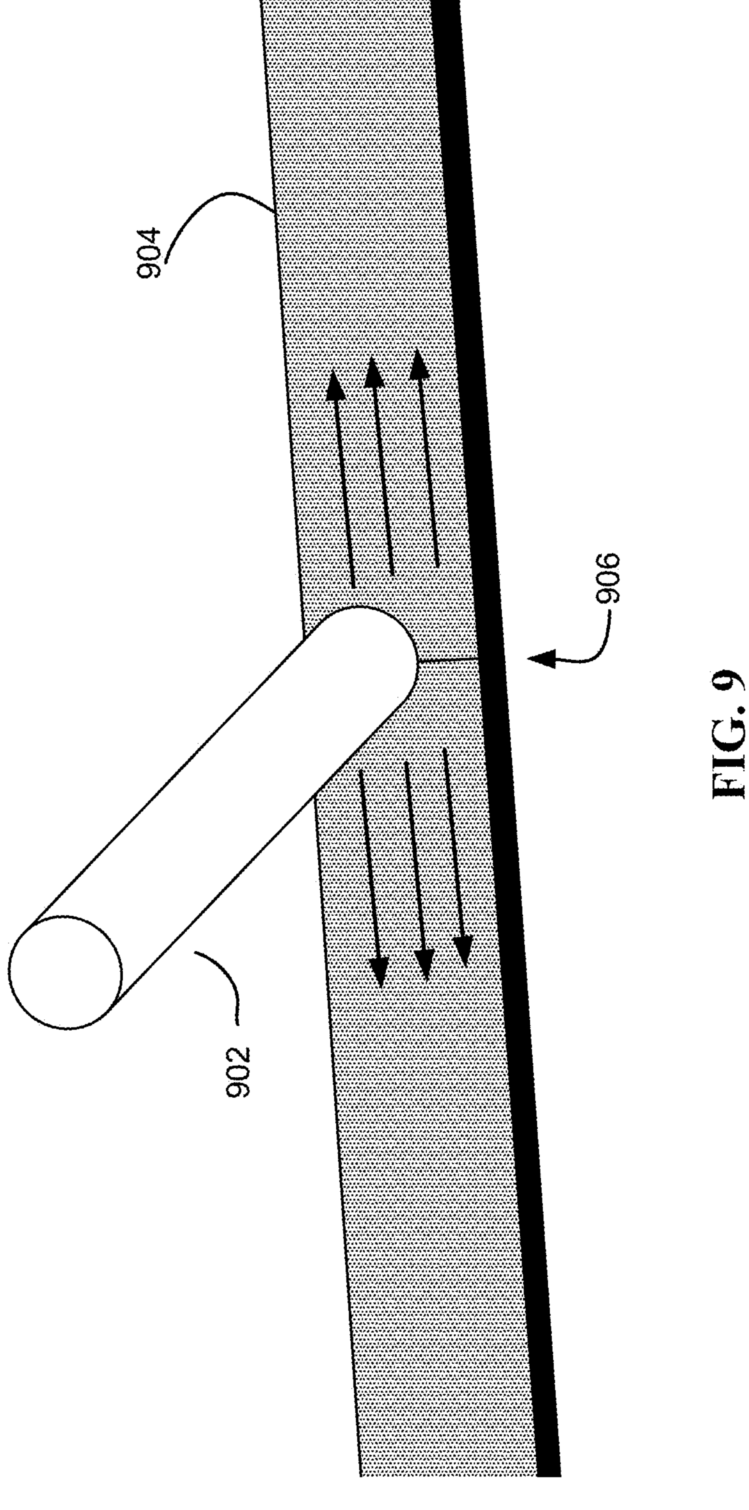
FIG. 9 shows an example geometry of a nitinol lead stub, according to one embodiment.

FIG. 9 shows an example geometry of a nitinol lead stub. In some embodiments, to reduce heat sink, copper (or silver) wires may be not directly attached to the ring. The copper wire may be connected to a nitinol lead stub that is welded onto the ring. The nitinol lead stubs may be made with an undersized diameter to make stubs hotter than the ring so that the nitinol lead stubs conduct more heat to the bottom of the ring during the capsular membrane cutting process. In the example shown in FIG. 9. The nitinol lead stub 902 is butt welded to the inner sidewall of the nitinol ring 904 at the connection joint 906 of the nitinol wire. The connection joint 906 of the nitinol wire is a weld joint that closes the ring. The nitinol lead stub 902 may be welded on over the connection joint 906 at the middle point of the connection joint 906 to provide equal currents in both directions around the nitinol ring 904, as indicated by the arrows in FIG. 9. In this way, no current flows vertically to the bottom edge of the ring along the connection joint 906, so the connection joint 906 may be heated by thermal conduction during and after the discharge, but not heated by electrical currents. In some implementations, the nitinol wire may be first welded to obtain the closed nitinol ring 904 and then the nitinol lead stub 902 may be butt welded on the nitinol ring 904. Alternatively, the two welding processes may be performed simultaneously. In one example, a nitinol wire may be of 0.5-1 mm long. The nitinol lead stub is configured to connect copper wires. When in use, the temperature of the nitinol lead stub may be increased, and the nitinol ring is isolated from the copper heat sink.

Figures 10A, 10B:
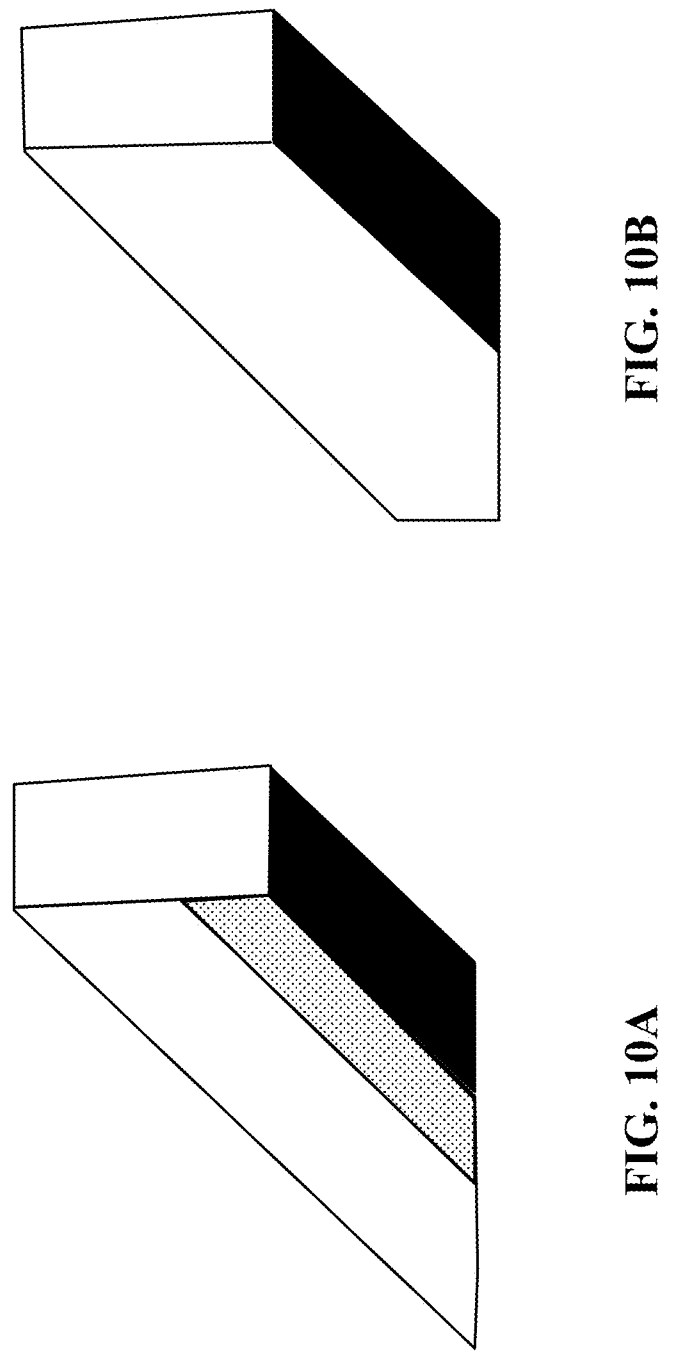
FIG. 10A and FIG. 10B show example nitinol wires with one or more sides coated with copper, according to one embodiment.

FIG. 10A and FIG. 10B show example nitinol wires with one or more sides coated with copper. Copper (or other high conductivity metal such as silver, gold, molybdenum, etc.) may be used to concentrate the heat at the capsular membrane. A highly conductive metal may be applied to the nitinol ring to concentrate power dissipation in specific parts of the ring. The electrical conductivity of copper is about 56 times that of nitinol. That means that if a thin strip of copper is added to the nitinol ring, then a significant amount of the electrical current will go through the copper. The current density in the copper will be about 56 times the current density in the nitinol. Therefore, a significant fraction of the power will be dissipated in the copper. This strategy is known in the prior art, but not feasible due to the expense of implementing it because it requires complicated masking of a ring-shaped structure to confine the copper to the desired locations. The present disclosure provides a low-cost way to actually use the strategy since coating is to be done on straight continuous lengths of wire.

As shown in FIG. 10A, the nitinol wire may be processed to have a rectangular cross section and at least portions of two sides of the nitinol wire are coated with copper. In some implementations, the nitinol wire may be coated with copper before it is bended to form a nitinol ring. The coated copper layer may have a thickness of 0.001-0.003 mm. For example, 2 micrometers of copper may be plated on a sputtered seed layer to coat the nitinol wire. Alternatively, the entire 2 micrometers of copper could be deposited by sputtering on the surface of the nitinol wire. In one example, the wire may be sputtered to etch off its oxide, and then perform a sputter deposit to coat copper on the wire. In FIG. 10B, copper may be coated on the surface that is the bottom of the ring, e.g., in contact with the capsular membrane when in use. By placing copper at the bottom of the ring where it will contact the capsular membrane, the heat may be concentrated in the space where it is needed to cut the membrane. This means that the ring is not as sensitive to heat sinking effects of the “L” or “T” shaped tabs that don’t have current flow through them. Metals that may be used for this purpose besides copper include gold, silver, tantalum, and molybdenum, among other metals.

In some embodiments, a nitinol wire is entirely coated with copper (e.g., 1-2 micrometer thickness of copper coating on a 0.0127-0.025 mm diameter nitinol wire) without masking. The wire may be seam welded to another nitinol wire of the structure, and the heat will be concentrated at the membrane. In some implementations, a straight wire may be sputter coated from just one side by simply allowing one half of the wire to be shadowed by the half that is facing the sputter target, as shown in FIG. 10B. In one example, copper may be sputtered on half of the circumference of a nitinol wire with an adhesion layer (100-1000 angstroms titanium), a diffusion barrier (100 to 1000 angstroms tantalum), and a plating seed layer (100 to 1000 angstroms copper). In some embodiments, the copper may be plated or sputtered on the nitinol wire. As an example for sputtering, the roll of wire may be in a load-lock of the sputtering system. After the system is pumped down to high vacuum, a transport system pulls the end of the wire to the take-up reel where it becomes engaged such that the rotating take-up reel proceeds to pull the wire past the sputtering targets. In some implementations, the nitinol wire may be run through a plating bath to apply a desired thickness of copper (for example 2 micrometers). If the entire copper is deposited by sputtering (without plating), the nitinol wire may be covered by an oxygen barrier (e.g., 50 to 1000 angstroms of molybdenum) that is biocompatible and has a high melting point.

In some embodiments, since the wire is straight, a physical slot may be used to shadow the deposition such that copper (or other types of coating material) is only deposited on the desired part of the wire as it goes past the sputtering target. This may be applied to wires of any cross-sectional shape (e.g., round, rectangular). In some embodiments, most of the power is dissipated by the copper coated wire(s), the nitinol support structure does not get as hot, and heat sinking by tabs is not as important. Therefore, simple single point of attachment tabs may be welded on the wires. Heat sinking by the tabs is further reduced by the use of nitinol wire with a smaller diameter to make the tabs.

In some embodiments, a tab may be brought in as a piece of preformed nitinol wire to be welded to the ring at a notch. The purpose of the notch may be to maintain the correct current density in the ring (in combination with the correct length and cross-sectional area of the nitinol tab). In this way, the tab provides a resistance equal to the resistance that would have been provided by the metal that was ground away to create the notch. This may be called a “loop tab” since it forms a closed loop with the ring. Unlike the “T” or “L” shaped tabs which are not heated directly by current flow through them, the loop tab has current flow through it so it will not create a cold spot. In some implementations, tabs may be made by grinding a notch in the wire to a predetermined depth (e.g., 0.05 mm) and then welding a preformed piece of nitinol wire having length and diameter that provides the same resistance that the missing metal had. In this way, the tabs may maintain the constant current density to avoid hot or cold spots. In one example, the length of the tab wire is greater than the length of the notch ground in the ring, the current carrying cross sectional area of the wire is greater than the cross-sectional area of the missing metal it replaces. For example, a ring height may be 0.150 mm, a ring thickness may be 0.075 mm, and a notch length may be 0.75 mm. The tab wire length may be 1.25 mm with tab wire diameter of 0.089 mm.

In some embodiments, the tabs may be formed by piercing and stretching and may be longer and thinner than the original material, thus having a higher resistance. As a result, the current density in the tab will be lower, and the current density in the ring below will be higher, resulting in a hot spot in the ring there. To mitigate this hot spot, negative feedback may be used to create less current flowing through the hotspot as it heats up and more current flowing through the tab which is electrically in parallel. Alternatively, the resistance may be corrected by welding on a piece of nitinol wire having the length and cross-sectional area needed to make the electrical resistance of the path through the tab equal to the resistance that would have been due to the original metal prior to piercing.

ADDITIONAL CONFIGURATION INFORMATION

The foregoing description of the embodiments of the disclosure has been presented for the purpose of illustration; it is not intended to be exhaustive or to limit the disclosure to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims. As used herein any reference to “one embodiment” or “an embodiment” means that a particular element, feature, structure, or characteristic described in connection with the embodiment is included in at least one embodiment. The appearances of the phrase “in one embodiment” in various places in the specification are not necessarily all referring to the same embodiment.

What is claimed is:

1. A method comprising:

compressing a nitinol wire with a circular cross-section on a first side of the nitinol wire and a second side of the nitinol wire opposite the first side to produce permanently flattened edges on the first side and the second side of the nitinol wire of at least a threshold width;

cutting off a portion of the nitinol wire on a third side of the nitinol wire and a fourth side of the nitinol wire opposite the third side to produce flattened edges on the third side and the fourth side of the nitinol wire of at least a threshold height to produce a modified nitinol wire with a rectangular cross section;

bending the modified nitinol wire into a ring shape such that a first end of the modified nitinol wire aligns with a second end of the modified nitinol wire;

permanently coupling the first end to the second end to produce a nitinol ring; and coupling the nitinol ring to a capsulotomy device such that the nitinol ring, upon receiving current flow from the capsulotomy device, produces heat sufficient to cut tissue in contact with the nitinol ring.

2. The method of claim 1, wherein permanently coupling the first end to the second end comprises:

welding the first end and the second end at a weld joint that closes the nitinol ring; and filing down the weld joint to produce a smooth seam.

3. The method of claim 2, wherein welding the first end and the second end comprises one or more of electrical resistance welding, laser welding, electron beam welding, percussive welding, ultrasonic friction welding, and diffusion bonding.

4. The method of claim 1, further comprising:

permanently coupling at least two leads to opposite sides of the nitinol ring.

5. The method of claim 4, wherein one of the at least two leads is coupled to a seam formed at the permanently coupled ends of the nitinol ring.

6. The method of claim 1, further comprising:

welding a nitinol lead stub on a middle point of a seam formed at the permanently coupled ends of the nitinol ring to provide equal currents in both directions around the nitinol ring.

7. The method of claim 1, further comprising:

coating one or more sides of the nitinol ring with copper.

8. The method of claim 1, further comprising:

coupling one or more tabs to a top side of the nitinol ring, wherein a bottom side of the ring is configured to be in contact with a capsular membrane.

9. The method of claim 1, wherein a cross section of the nitinol ring is within a threshold range throughout an entirety of the nitinol ring.

10. The method of claim 1, further comprising:

annealing the nitinol ring at a predetermined temperature to obtain a super elastic state of the nitinol ring.

11. A capsulotomy device, comprising:

a suction cup; and a super elastic nitinol ring coupled to the suction cup and configured to, upon receiving current flow from the capsulotomy device, produce heat sufficient to cut tissue in contact with the nitinol ring, wherein the nitinol ring is manufactured by:

permanently flattening edges on a first side and a second side opposite the first side of a nitinol wire of at least a threshold width, wherein the nitinol wire has a circular cross section, and wherein the flattened edges on the first side and the second side are formed by compressing the nitinol wire on the first side of the nitinol wire and the second side of the nitinol wire;

flattening edges on a third side and a fourth side opposite the third side of the nitinol wire of at least a threshold height, wherein the flattened edges on the third side and the fourth side are formed by cutting off a portion of the nitinol wire on the third side of the nitinol wire and the fourth side of the nitinol wire, producing a modified nitinol wire with a rectangular cross section;

and producing the nitinol ring by bending the modified nitinol wire such that a first end of the modified nitinol wire aligns with a second end of the modified nitinol wire and permanently coupling the first end to the second end of the modified nitinol wire.

12. The device of claim 11, wherein the first end and the second end of the modified nitinol wire are welded at a weld joint that closes the nitinol ring, and weld point is filed down to produce a smooth seam.

13. The device of claim 12, wherein welding the first end and the second end comprises one or more of electrical resistance welding, laser welding, electron beam welding, percussive welding, ultrasonic friction welding, and diffusion bonding.

14. The device of claim 11, further comprising:

at least two leads that are permanently coupled to opposite sides of the nitinol ring.

15. The device of claim 14, wherein one of the at least two leads is coupled to a seam formed at the permanently coupled ends of the nitinol ring.

16. The device of claim 11, further comprising:

a nitinol lead stub welded on a middle point of a seam that is formed at the permanently coupled ends of the nitinol ring, the nitinol lead stub configured to provide equal currents in both directions around the nitinol ring.

17. The device of claim 11, further comprising:

copper coating on one or more sides of the nitinol ring.

18. The device of claim 11, further comprising:

one or more tabs coupled to a top side of the nitinol ring, wherein a bottom side of the ring is configured to be in contact with a capsular membrane.

19. The device of claim 11, wherein a cross section of the nitinol ring is within a threshold range throughout an entirety of the nitinol ring.

20. The device of claim 11, wherein the nitinol ring is annealed at a predetermined temperature to obtain a super elastic state of the nitinol ring.

* * * * *